United States Patent
Fried et al.

(10) Patent No.: US 9,907,616 B1
(45) Date of Patent: Mar. 6, 2018

(54) SYSTEM FOR TFL LITHOTRIPSY, INCLUDING ENDOSCOPE WITH DETACHABLE AND REPLACEABLE WAVE GUIDE AND METHOD FOR USE

(71) Applicants: The University of North Carolina at Charlotte, Charlotte, NC (US); The Charlotte Mecklenburg Hospital Authority, Charlotte, NC (US)

(72) Inventors: Nathaniel Michael Fried, Concord, NC (US); Richard Leious Blackmon, Charlotte, NC (US); Pierce Butler Irby, III, Charlotte, NC (US); Thomas Clifton Hutchens, Yadkinville, NC (US)

(73) Assignees: University of North Carolina at Charlotte, Carlotte, NC (US); The Charlotte Mecklenburg Hospital Authority, Charlotte, NC (US)

( * ) Notice: Subject to any disclaimer, the term of this patent is extended or adjusted under 35 U.S.C. 154(b) by 83 days.

(21) Appl. No.: 14/181,611

(22) Filed: Feb. 14, 2014

Related U.S. Application Data

(63) Continuation-in-part of application No. 13/752,893, filed on Feb. 19, 2013, now abandoned.
(Continued)

(51) Int. Cl.
*A61B 18/20* (2006.01)
*A61B 18/26* (2006.01)
(Continued)

(52) U.S. Cl.
CPC .... *A61B 18/26* (2013.01); *A61B 2017/00296* (2013.01); *A61B 2018/00505* (2013.01);
(Continued)

(58) Field of Classification Search
CPC ......... A61B 18/20; A61B 18/22; A61B 18/26; A61B 2018/263; A61B 2018/266;
(Continued)

(56) References Cited

U.S. PATENT DOCUMENTS

| 4,538,609 A | * | 9/1985 | Takenaka | A61B 18/22 385/147 |
| 4,830,462 A | * | 5/1989 | Karny | A61B 18/22 385/125 |

(Continued)

OTHER PUBLICATIONS

Fried, Nathaniel M., Thulium Fiber Laser Lithotripsy: An In Vitro Analysis of Stone Fragmentation Using a Modulated 110-Watt Thulium Fiber Laser at 1.94, Lasers Surgery Medicine 37:53-58, 2005.

(Continued)

*Primary Examiner* — Ahmed Farah
(74) *Attorney, Agent, or Firm* — Clements Bernard Walker PLLC; Christopher L. Bernard

(57) ABSTRACT

A system for use in TFL lithotripsy procedures uses a silica trunk fiber semi-permanently mounted in an endoscope and includes a detachable and replaceable wave guide treatment tip, including hollow wave guides and fiber tips. The system provides for ready removal and replacement of wave guides damaged during lithotripsy. The trunk fiber in the endoscope tube is of diameter ≤200 μm, suitable for use in the lower pole of the kidney, and should be useful over-and-over with only the detachable wave guide removed and replaced, whether during a single procedure or for multiple procedures on different patients in which the endoscope tube and trunk fiber are sterilized between patients. Multiple connector assemblies are provided for optical coupling contact between the detachable wave guide and trunk fiber and include a gap for dissipation of heat between the trunk fiber and the wave guide when in optically coupling contact.

11 Claims, 14 Drawing Sheets

Related U.S. Application Data

(60) Provisional application No. 61/594,040, filed on Feb. 2, 2012.

(51) Int. Cl.
   *A61B 17/00* (2006.01)
   *A61B 18/00* (2006.01)
   *A61B 18/22* (2006.01)

(52) U.S. Cl.
   CPC .............. *A61B 2018/00511* (2013.01); *A61B 2018/00517* (2013.01); *A61B 2018/2205* (2013.01); *A61B 2018/2255* (2013.01)

(58) Field of Classification Search
   CPC ............ A61B 2018/201; A61B 18/245; A61B 18/00505; A61B 2018/00511; A61B 2018/00517; A61B 2018/2015; A61B 2018/2205; A61B 2018/2227; A61B 17/00234; A61B 2017/00296; A61B 2017/1205
   USPC ......... 606/1, 2.5, 130, 13–16; 600/101, 105, 600/108, 127, 135, 172, 175, 182
   See application file for complete search history.

(56) References Cited

U.S. PATENT DOCUMENTS

| | | | |
|---|---|---|---|
| 4,895,145 A * | 1/1990 | Joffe | A61B 18/20 606/11 |
| 5,163,935 A * | 11/1992 | Black | A61N 5/0601 600/108 |
| 5,570,445 A * | 10/1996 | Chou | G02B 6/4296 385/78 |
| 7,090,411 B2 * | 8/2006 | Brown | G02B 6/4296 385/78 |
| 8,277,442 B2 * | 10/2012 | Di Sessa | A61B 18/22 606/1 |
| 8,419,293 B2 * | 4/2013 | Zerfas | G02B 6/4296 385/78 |
| 8,888,378 B2 * | 11/2014 | Zerfas | G02B 6/4296 385/76 |
| 9,125,677 B2 * | 9/2015 | Sobol | A61B 18/201 |
| 2006/0235270 A1 * | 10/2006 | Teichmann | A61B 1/00142 600/106 |
| 2009/0299352 A1 * | 12/2009 | Zerfas | A61B 1/00165 606/15 |
| 2010/0010314 A1 * | 1/2010 | Krattiger | A61B 1/00096 600/182 |
| 2012/0238821 A1 * | 9/2012 | Yoshida | A61B 1/00117 600/182 |

OTHER PUBLICATIONS

Nicholas J. Scott et al., Thulium Fiber Laser Ablation of Urinary Stones Through Small-Core Optical Fibers, IEEE Journal of Selected Topics in Quantum Electronics, vol. 15, No. 2, Mar./Apr. 2009.

Richard L. Blackmon et al., Thulium Fiber Laser Lithotripsy Using Tapered Fibers, Lasers in Surgery and Medicine 42:45-50, 2010.

Richard L. Blackmon et al., Holmium:YAG (2,120nm) Versus Thulium Fiber (1,908 nm) Laser Lithotripsy, Lasers in Surgery and Medicine 42:232-236, 2010.

Richard L. Blackmon et al., Comparison of Holmium:YAG and thulium fiber laser lithotripsy: ablation thresholds, ablation rates, and retropulsion effects, Journal of Biomedical Optics 16(7), 071403, Jul. 2011.

Richard L. Blackmon et al., Enhanced thulium fiber laser lithotripsy using micro-pulse train modulation, Journal of Biomedical Optics 17(2), 028002, Feb. 2012.

Richard L. Blackmon et al., Fiber-optic manipulation of urinary stone phantoms using holmium:YAG and thulium Fiber lasers, Journal of Biomedical Optics 18(2), 028001, Feb. 2013.

Thomas C. Hutchens et al., Detachable fiber optic tips for use in thulium fiber laser lithotripsy, Journal of Biomedical optics 18(3), 038001, Mar. 2013.

Thomas C. Hutchens et al., Hollow steel tips for reducing distal fiber burn-back during thulium fiber laser lithotripsy, Journal of Biomedical Optics 18(7), 078001, Jul. 2013.

Luke A. Hardy et al., Rapid Thulium Fiber Laser Lithotripsy at Pulse Rates up to 500 Hz Using a Stone Basket, IEEE Journal of Selected Topics in Quantum Electronics, vol. 20, No. 5, Sep./Oct. 2014.

* cited by examiner

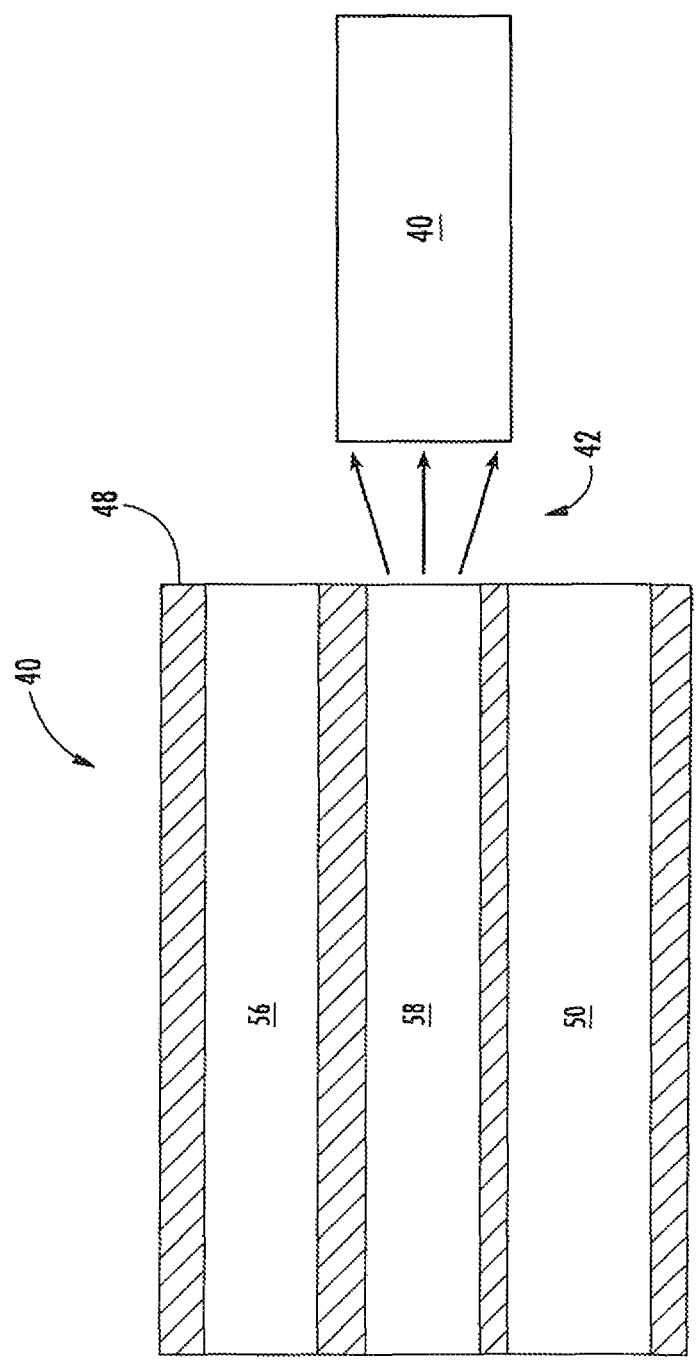

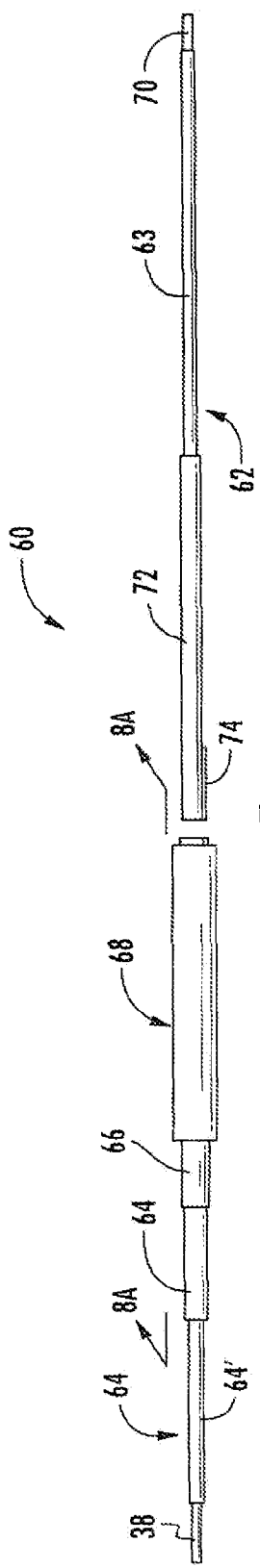
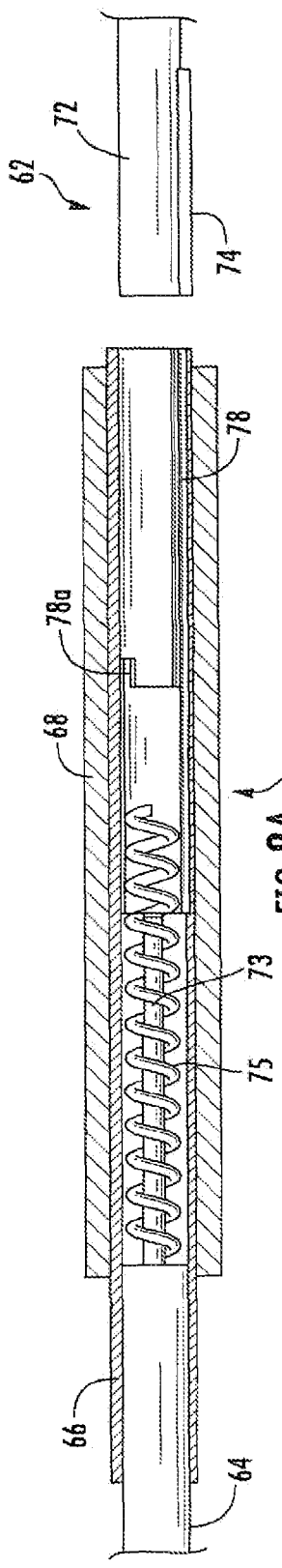
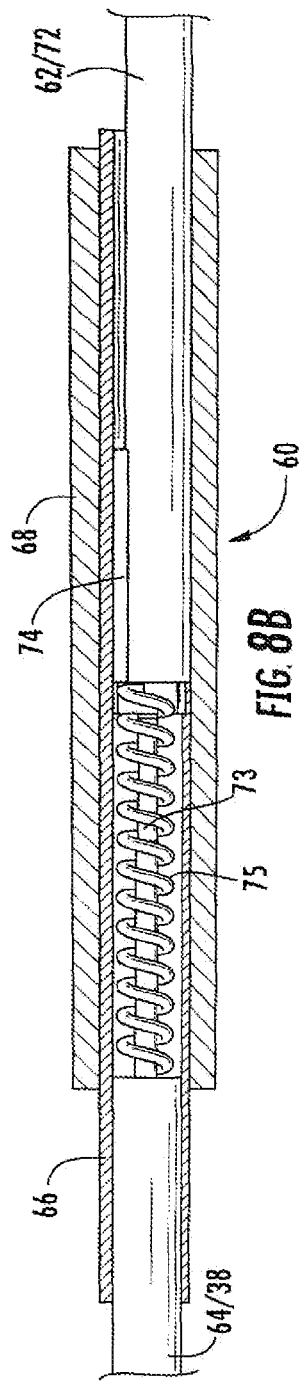
FIG. 7
FIG. 8A
FIG. 8B

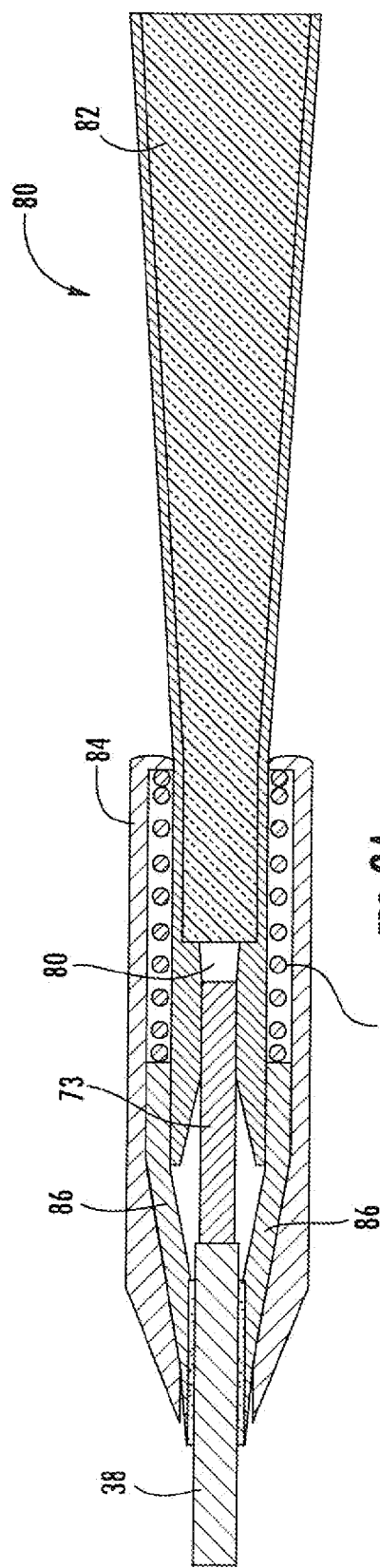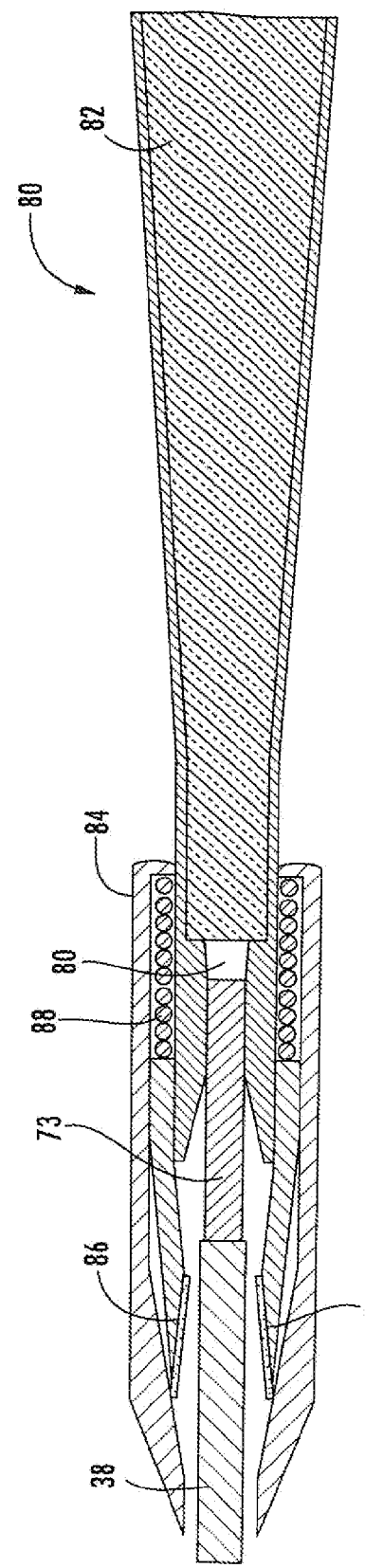

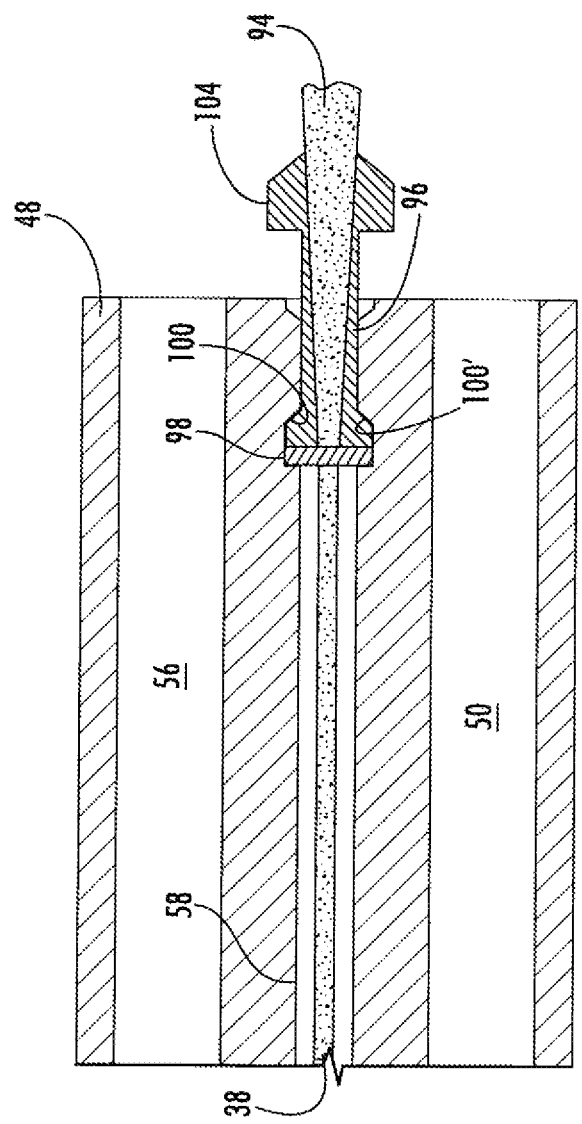

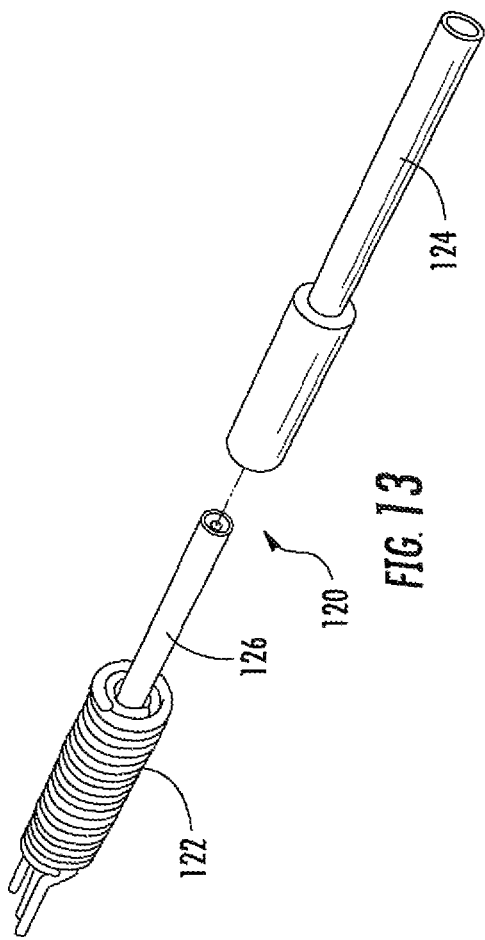
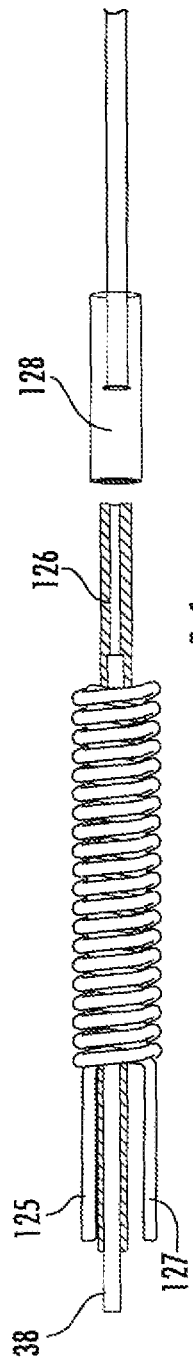
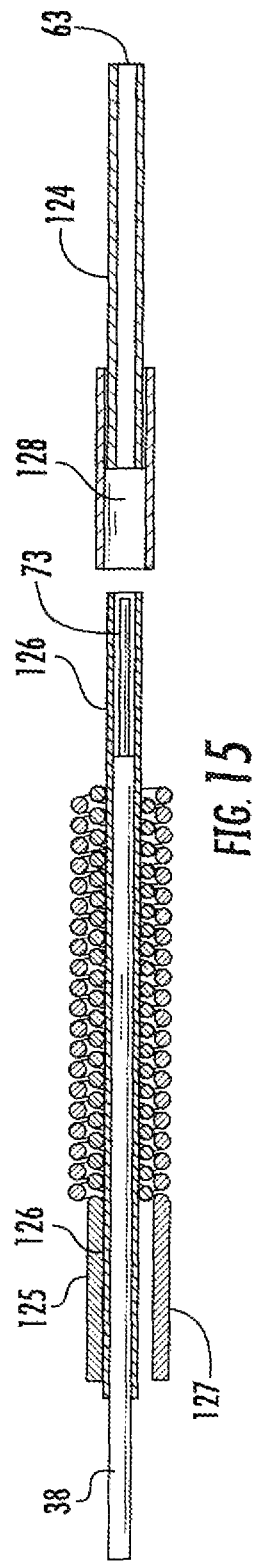
FIG. 13
FIG. 14
FIG. 15

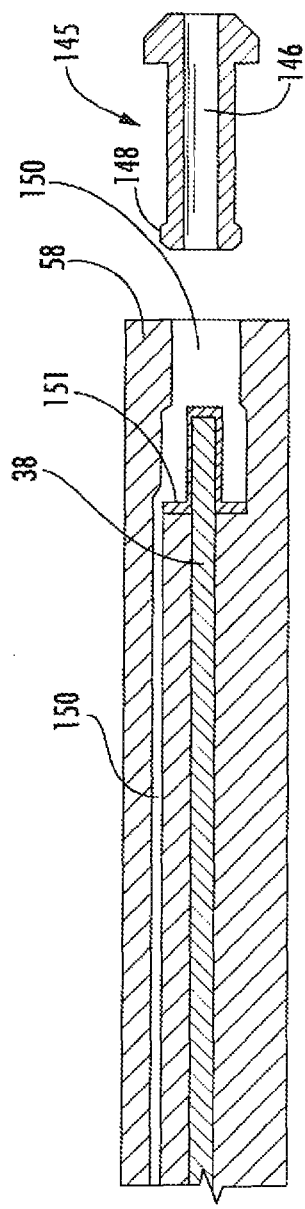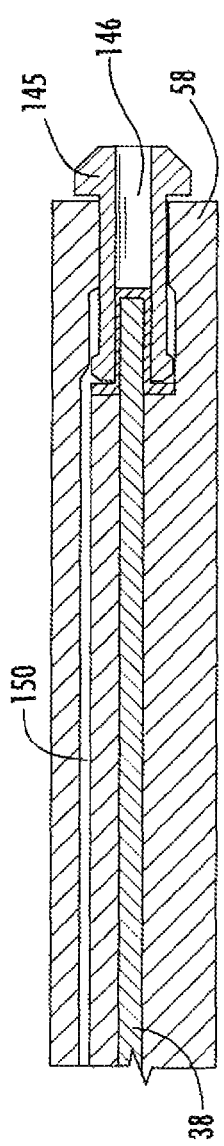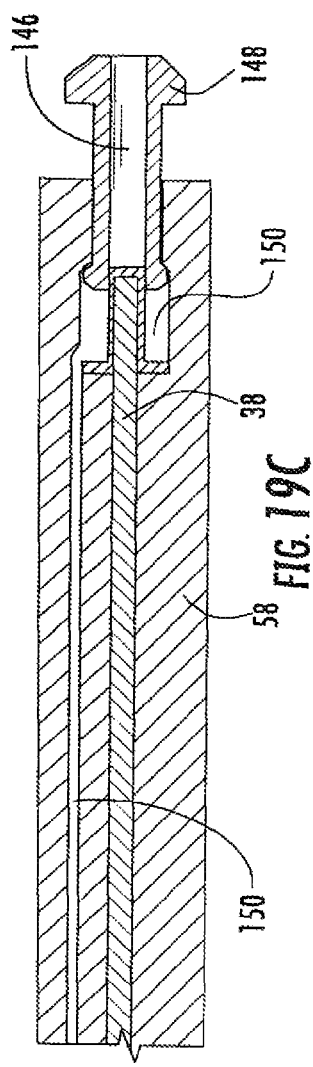

SYSTEM FOR TFL LITHOTRIPSY, INCLUDING ENDOSCOPE WITH DETACHABLE AND REPLACEABLE WAVE GUIDE AND METHOD FOR USE

FIELD OF THE INVENTION

The invention described herein relates to endoscopic lithotripsy using the thulium fiber laser ("TFL") for physical destruction of hardened masses in the body through minimally invasive techniques, most commonly for treatment of urinary stone disease. More specifically, the invention relates to the optical fiber used for TFL lithotripsy.

BACKGROUND OF THE INVENTION

It is estimated that 10% of the United States population will suffer from urinary stone disease during their lifetimes. The National Institute of Diabetes and Digestive and Kidney Diseases reports that more than 1 million cases occur annually. Patients often experience acute onset of intense pain as the first symptom of the presence of a hardened mass in the urinary tract, which typically lands them in the emergency room of a hospital. Evaluation and treatment of urinary stone disease costs billions of dollars annually.

Patients with small stones normally are advised to wait to pass the stone. For more severe urinary stone disease, physicians commonly perform a lithotripsy procedure in which the physician breaks apart stones that are too large to pass successfully. One typically employed method for removing large urinary tract stones is endoscopic lithotripsy, generally performed with an ureteroscope, which is a specialized fiber optic endoscope designed to navigate the urinary tract. The endoscope may have as one of its components an optical fiber of a length and flexibility to stretch from a laser at the proximal end of the fiber to the stone's location at the distal end of the fiber inserted into the urethra, bladder, or kidney. Once the treatment tip of the fiber is in close proximity or even in contact with the stone, energy is transmitted through the fiber to the stone.

Optical fibers normally comprise a core host material, a cladding, and a jacket. Typically, the treatment fiber that is connected to the laser system and inserted into the body comprises low-OH silica multimode fiber that includes a solid core of silica, a silica cladding of a different index of refraction to direct the light back into the core for propagation, and a polyimide buffer or other suitable plastic jacket. The core host is doped with an impurity that changes the refractive index of the core, trapping light in the core so that the light is transmitted axially. The silica core typically is doped with germanium. The cladding circumscribing the surface of the core directs light energy back into the core to propagate the light along the length of the fiber, which is commonly referred to as "total internal reflection." The jacket circumscribing the cladding protects the cladding and the core within, but does not aid in light transmission.

For endoscopic laser lithotripsy, many physicians use the Holmium:YAG (Ho:YAG) laser, which is a flashlamp pumped solid-state laser having within the laser housing a solid crystal lasing medium comprising a host of yttrium, aluminum, and garnet doped with holmium. The pump source stimulates the spontaneous and amplified emission of photons in the solid crystal lasing medium, providing energy to the laser system. The Ho:YAG laser provides a multipurpose system having a relatively high power output that can be used to cut or coagulate a variety of soft and hard tissues.

However, because flashlamps produce a broad spectrum of light, much of the energy is wasted as heat in the gain medium. Ho:YAG laser systems produce a laser beam that includes a relatively large and multimode beam waist, departing from the ideal single-mode Gaussian beam, and has only limited flexibility for pulse rate and duration. Problems may occur, including thermal lensing, potentially leading to misalignment of the laser beam with the proximal end of the treatment optical fiber, which is the treatment fiber input end attached to the laser source. Suboptimal coupling from the large multimode beam profile can damage the treatment fiber on the proximal end and the treatment fiber must then be replaced.

The Ho:YAG laser also tends to subject the distal, or treatment end, of the treatment fiber to damage, at least in part because the fibers are not sufficiently flexible to avoid damage from bending in the tight spaces of the urinary tract, particularly the lower pole of the kidney. Semi-rigid ureteroscopes typically use relatively large and somewhat less flexible 365 µm fibers. Flexible ureteroscopes normally have a single working channel of 1.2 mm inner diameter that provides limited valuable space for saline irrigation and thus typically are used with smaller fibers having a core no larger than 270 µm. Larger fibers can be accommodated, but reduce flexibility and limit saline irrigation. However, the Ho:YAG laser's large beam waist prevents optimal power coupling into fibers smaller than 270 µm. The short bending radius at the distal end of a 270 µm fiber decreases the longevity of these fibers. Over multiple cycles of bending the laser energy leaks from the core into the cladding to damage the fiber. Stone fragmentation can also damage the fiber on the distal end and the entire treatment fiber must then be replaced, even if the proximal end is yet undamaged.

Smaller fibers of about 200 µm or less could provide more flexibility, especially for accessing hard-to-reach locations in the lower pole of the kidney, and could provide more room in the working channel of the ureteroscope for irrigation with saline, which would improve visibility for the physician and safety for the patient. Nevertheless, optical coupling into these smaller fibers with the Ho:YAG laser's multimode beam profile risks overfilling of the input fiber core, launching laser energy into the cladding, and damaging the treatment fiber.

Proximal tapered fiber tips, in which the fiber has a steep taper at the proximal end from a larger diameter to a smaller trunk diameter, have been used to more efficiently couple Ho:YAG laser energy into fibers with smaller trunk diameters. However, higher order modes are created once the small core size is reached at the distal end of the taper. These modes fall outside the total internal reflection condition of the fiber. Laser energy typically escapes into the fiber cladding, potentially degrading fiber integrity. With extremely tight bending of the fiber, such as with ureteroscope deflection into the lower pole of the kidney, these leaking modes may increase and laser energy may escape. Escaping laser energy can burn through the ureteroscope wall, damaging the ureteroscope and potentially harming the patient.

Single use and reusable treatment fibers are available for Ho:YAG laser lithotripsy, with 270 µm fibers common in flexible ureteroscopes and the even larger 365 µm fibers common in semi-rigid ureteroscopes. Procedures for reuse include stripping the fiber jacket, cleaving the tip, and sterilizing the fiber after each procedure. Reprocessing for reuse costs little compared to replacement of single use fibers. Reusing Ho:YAG laser lithotripsy fibers by cleaving the damaged tip has been reported to decrease single procedure costs by an average of $100 US. Reusable fibers are not typically discarded until they become too short after multiple cleavings or they become irreparably damaged from bending or suboptimal coupling.

The thulium fiber laser (TFL), which uses a thulium doped silica fiber as the lasing medium instead of the holmium doped crystal of yttrium, aluminum, and garnet, has been proposed as an alternative laser lithotripter to the clinical Ho:YAG laser for several reasons. First among them is that the TFL has 4 times higher absorption in tissues at equivalent pulse energies compared to the Ho:YAG laser, which means that the TFL can ablate stones at 4 times lower pulse energies than the Ho:YAG laser. The TFL is pumped with a laser diode energy source instead of a flashlamp, which provides for a more efficient energy transfer to the optical fiber. Generally speaking, flashlamp pumped lasers, including the Ho:YAG laser, are limited to fixed pulse lengths at lower pulse rates than the TFL. The TFL is more compact than the Ho:YAG laser and can be electronically triggered to operate at nearly any pulse length or configuration. The TFL can be modulated to create pulse trains. The micropulse train, also called a "pulse packet" mode of operation, enables increased laser ablation rates for both soft tissues and hard tissues, including urinary stones, for the TFL as compared to the Ho:YAG laser.

The TFL has a higher absorption coefficient and shorter optical penetration depth in water. The TFL absorption coefficient is 160 cm$^{-1}$ compared to 28 cm$^{-1}$ for the Ho:YAG laser. The most common urinary stones are hydrates, and the stones typically are immersed in a fluid environment, including saline irrigation that is used to improve visualization during lithotripsy. Water absorption is an important factor even though urinary stones typically have significantly less bound water content than soft tissues. Water absorption of laser energy is correlated with the ablation threshold and is dependent on the wavelength of the laser. The TFL has two major emission wavelengths at 1908 and 1940 nm, which closely match both a high and low temperature water absorption peak, respectively. The TFL absorption peak shifts from 1940 nm at room temperature to 1910 nm at the higher temperatures encountered when water associated with urinary stones is superheated during laser tissue ablation, including both water bound in the stone and unbound water surrounding the stone.

Another advantage of the TFL is its Gaussian spatial bean profile compared to the Ho:YAG laser's multimode beam. The superior spatial beam profile of the TFL improves coupling and transmission of laser power through smaller diameter treatment fibers for lithotripsy, allowing use of fibers of core diameters of from about 200 µm or less. This reduction in fiber cross-section would be expected to allow for increased ureteroscope deflection and higher saline irrigation rates through the working channel, which, in turn, could reduce procedure times, probability of ureteroscope damage, and physician visibility, improving patient safety. However, the smaller diameter distal fiber tips on the treatment fiber have been shown to degrade and suffer from "burn-back" more than larger diameter fiber tips, which means the entire fiber has to be replaced more frequently during the procedure.

The TFL's Gaussian beam profile, which is an indication of the spatial intensity, width and quality of the laser beam, provides improved coupling into small treatment fibers, eliminating proximal fiber tip damage as compared to the Ho:YAG. By reversing the typical orientation of the tapered fiber, and using the increasing taper and larger core at the distal output end instead of the laser proximal input end, the distal tip of the continuous treatment fiber has been shown to be more damage resistant during lithotripsy. The benefits of a small-core trunk fiber, including increased irrigation and flexibility, are then combined with that of a robust larger-core distal fiber tip. The tip can be extended from the ureteroscope into contact with the stone, while also providing sufficient irrigation since only the small-core trunk fiber remains within the working channel of the ureteroscope. Other potential advantages of a small trunk fiber having a tapered distal fiber tip include less divergence of the output beam and a larger treatment area.

Nevertheless, fiber tip damage and burn-back still occur with large tips and the entire fiber must be replaced or repaired during or after the procedure, so impediments remain to adoption of the TFL for lithotripsy.

It would be desirable to provide an ureteroscope in combination with a fiber delivery system that has the advantages of a TFL of compact size, increased ablation rates at lower energies, improved irrigation, reduced damage at the proximal end in alignment with the laser source, and reduced fiber tip damage at the distal end of the treatment fiber, and yet eliminates or otherwise improves upon the disadvantages currently experienced, including the problems of burn-back, fiber replacement during or after each procedure, and fiber reconditioning for reuse.

SUMMARY OF THE INVENTION

The invention improves fiber longevity, procedure performance, and customization of TFL lithotripsy, in part by providing a detachable and replaceable wave guide tip for a "tipless" trunk portion of a treatment fiber in the endoscope. The tipless trunk fiber never directly contacts the urinary stone or other hardened mass and can be reused multiple times without cleaving a tip. The trunk fiber can be semi-permanently integrated into the endoscope tube. The reusable trunk fiber used in accordance with the invention does not normally require replacement or repair while lithotripsy is being performed or even after the procedure and typically can be used for multiple procedures, sterilized in place in the ureteroscope or other endoscope between procedures, and for different patients. The invention also enables a physician to use a smaller fiber regardless of the preselected energy output.

The detachable and replaceable wave guide tip for the tipless trunk fiber, which is the portion that supplies energy to the urinary stone or other hardened mass, may be a fiber or a hollow wave guide, cylindrical or tapered. In one embodiment, the invention provides a detachable and disposable large-core distal fiber tip for optical coupling contact, but not necessarily physical contact, with a reusable smaller-core trunk fiber. A small gap is typically maintained between the disposable tip and the reusable trunk fibers to reduce the potential for heat damage in energy transfer, so the disposable tips and reusable trunk fibers are in optical coupling contact, but not direct physical contact in which the ends are touching. These embodiments of the invention take advantage, in part, of the more frequent tip damage and burn back that occurs in smaller, more flexible fibers by enabling the physician to readily and easily exchange disposable tips while the procedure is being performed, thus obtaining the advantages of TFL lithotripsy, improving flexibility of operation, and mitigating the drawbacks, especially those associated with fiber tip damage.

The assembly for optically connecting the disposable tip to the reusable trunk fiber should be of diameter ≤1 mm, which can fit into the working channel of a flexible ureteroscope and still provide adequate space for fluid for irrigation. Alternatively, the trunk fiber can be mounted in its own dedicated channel or in an illumination or camera channel. The disposable tip can be rapidly removed and replaced as needed by a urologist during the procedure, and the disposable tips, connecting assembly, and reusable trunk fibers can be mass produced at low cost.

The invention includes the disposable and detachable wave guide tips and a separate small-core trunk fiber integrated within an ureteroscope or other endoscope for multiple uses, assembly of the detachable wave guide and small-core trunk fiber, and methods for performing TFL lithotripsy using the assembly of the invention. The method includes the steps of selecting the wave guide, providing a distal end core diameter correlated to an energy output area for improved control and customization of energy output, optically connecting the disposable wave guide to the trunk fiber in the endoscope, and performing endoscopic TFL lithotripsy, most commonly removal of urinary tract stones with an ureteroscope.

The tip-to-trunk fiber optical coupling connection of the invention, of a multiple-use smaller-core trunk fiber to a single-use, disposable, larger-diameter treatment tip, is a low profile and easily detachable interface that, in its principal aspect, provides efficient light energy transmission from the distal end of the trunk fiber to the proximal end of the tip and from the distal end of the tip to the urinary stone. Transmission is equivalent or near equivalent to that of the prior art, continuous, one-piece fiber with a distal tip, in both cylindrical and tapered formats, and yet overcomes significant drawbacks by providing easily replaceable, disposable detachable tips and reusable trunk fibers.

In a more specific embodiment among several available structures for achieving the above results, a spring-loaded twist locking mechanism provides the tip-to-trunk fiber optical coupling connection between a trunk fiber and a cylindrical or tapered fiber tip. In another embodiment, the proximal end of a highly polished fiber tip is inserted into a receiving sleeve mounted on the distal end of a highly polished trunk fiber and in optical coupling contact, which is to say light energy transmitting contact, with the trunk fiber. In yet another embodiment, a fiber tip is mounted into a threaded micro-ferrule for mating threaded engagement with a corresponding ferrule mounted on the distal end of the trunk fiber. In yet another embodiment, the fiber tip may be magnetically mounted into the endoscope tip in optical coupling contact with the trunk fiber. In still other embodiments, the tip is a hollow wave guide mounted in a plug-like sleeve for insertion into the distal end of the ureteroscope in light-transmitting contact with the trunk fiber mounted within the ureteroscope. In other embodiments, the tip of the endoscope, including the treatment tip optically connected to the trunk fiber can be detached, the treatment tip replaced, and the endoscope tip reinserted.

The treatment tip can comprise a low-OH silica fiber tip of the same composition as the trunk fiber or a hollow wave guide for snapping into the end of the distal end of the endoscope and into optically transmitting contact with a recessed trunk fiber. It should be recognized that the fiber tip wave guide is subject to burn back in use and is designed to be easily replaceable so that the trunk fiber can be used over and over. Lithotripsy is an inherently violent process. A hollow wave guide may be damaged during lithotripsy and is also subject to replacement so that the trunk fiber can be used over and over. The hollow wave guide may comprise, for example, a hollow low-OH silica core with a reflective lining or a hollow stainless steel tubular core with a highly polished inner surface.

The trunk fiber diameter normally ranges from about 50 to 200 μm in diameter, and more typically from about 100 to 150 μm, providing ultimate flexibility for the lithotripsy procedure and ease of entry into the lower pole of the kidney or other tight bodily cavities multiple times without damaging the trunk fiber and without having to replace the trunk fiber. Depending on the ureteroscope or other endoscope length, the trunk fiber may vary in length from about 0.5 to 2 meters.

The disposable, single-use, treatment tips may vary in diameter from 100 to 600 μm and from less than 0.5 to 5 cm in length, most commonly from 5 to 10 mm in length. The proximal end of a detachable wave guide tip, including a hollow wave guide tip or a fiber tip that is in optical transmitting contact with the distal end of the small diameter trunk fiber, is generally of a size to efficiently transfer light energy from the distal end of the trunk fiber through the tip to the distal end of the tip and then to the stone or other hardened mass. Thus, the proximal end of the wave guide, in optical coupling contact with the distal end of the trunk fiber, will be of size compatible for efficient optical coupling with the trunk fiber. The disposable tip may be either cylindrical, in which event the proximal and distal ends are of similar diameter, typically about 300 μm in diameter, or tapered, in which case the distal end normally is of larger diameter than the proximal end. Typically, for a tapered tip, the ratio of the proximal to the distal end will be in a range of from about 1:2 to 1:3. For example, the detachable tip may have a proximal end of 100 μm and a distal end of about 200 μm to 300 μm. If the proximal end is 200 μm, then the distal end will be from 400 to 600 μm. The wider distal end of the tip provides a means to modify laser divergence to improve energy delivery to ablate a hardened mass, including a kidney stone.

Thus, the invention provides an ureteroscope with a semi-permanent mounted trunk fiber intended for use for multiple TFL procedures for ablating hardened masses in the urinary tract, including, for example, ablation of kidney stones. The smaller core reusable silica trunk fiber provides for improved irrigation during the procedure, whether mounted in the working channel of an endoscope or another channel, compared to the larger core silica fibers of the Holmium:YAG laser, normally mounted in the working channel. Treatment tips comprising hollow wave guides or disposable, single-use, larger-diameter fiber tips, cylindrical or tapered, and optically connected to the trunk fiber at the distal end of the trunk fiber, allow ready replacement of tips damaged during the procedure and for new tips for each subsequent procedure. Urologists desiring faster TFL lithotripsy procedures can rapidly replace damaged, detachable distal fiber tips and customize lithotripsy without concern about the laser-to-trunk fiber connection.

BRIEF DESCRIPTION OF THE DRAWING

FIG. 6 is a highly schematic side sectional view of an endoscope cap of the invention taken through the vertical centerline of FIG. 4;

FIG. 7 illustrates a partially exploded plan view of one embodiment of an optical fiber assembly of the invention for spring-loaded, twist-locking, keyed insertion and release of a detachable fiber tip for lithotripsy;

FIG. 8A illustrates the connector assembly of FIG. 7 in additional detail, including a section through the assembly taken along lines 8-8 of FIG. 7;

FIG. 8B illustrates the partial section of FIG. 8A in assembled relation;

FIG. 9A illustrates a sectional view of an assembly of a self-centering spring-loaded retaining sleeve for a detachable fiber tip and trunk fiber of the invention;

FIG. 9B illustrates the sectional view of the assembly of FIG. 9 prior to complete assembly and retention by the spring-loaded sleeve;

FIG. 10B illustrates the tapered tip and end cap of FIG. 10A in assembled relation;

FIG. 13 illustrates a perspective and exploded view of an embodiment providing for securing a detachable tip fiber to a trunk fiber by electromagnetic attachment;

FIG. 14 illustrates a plan perspective and partial longitudinal sectional view of the exploded assembly of FIG. 13;

FIG. 15 illustrates a longitudinal sectional view through the exploded plan view of FIG. 14;

FIG. 19A illustrates a longitudinal section through an exploded view of a detachable hollow wave guide tip of the invention and an end cap for an endoscope having an axially centrally-located trunk fiber where the detachable wave guide tip is to be retained in a mated receiving sleeve adjacent the distal end of the trunk fiber and having a pneumatic channel for supplying air to the wave guide to extend the wave guide tip axially from the end cap during use;

FIG. 19B illustrates the embodiment of FIG. 19A fully assembled and in the absence of pneumatic power to secure the wave guide; and FIG. 19C illustrates the embodiment of FIG. 19B having pneumatic power applied to secure and extend the wave guide beyond the distal surface of the endcap.

Corresponding reference characters indicate corresponding parts throughout the several views of the drawings, with similar parts indicated by primes.

DETAILED DESCRIPTION

The invention will now be described more fully hereinafter with reference to the accompanying drawings in which are illustrated some, but not all, of the concepts of the invention. Indeed, the invention may be embodied in many different forms and should not be construed as limited to the examples set forth herein; rather, the embodiments provided in this disclosure are intended to satisfy applicable legal requirements.

Figure 1:
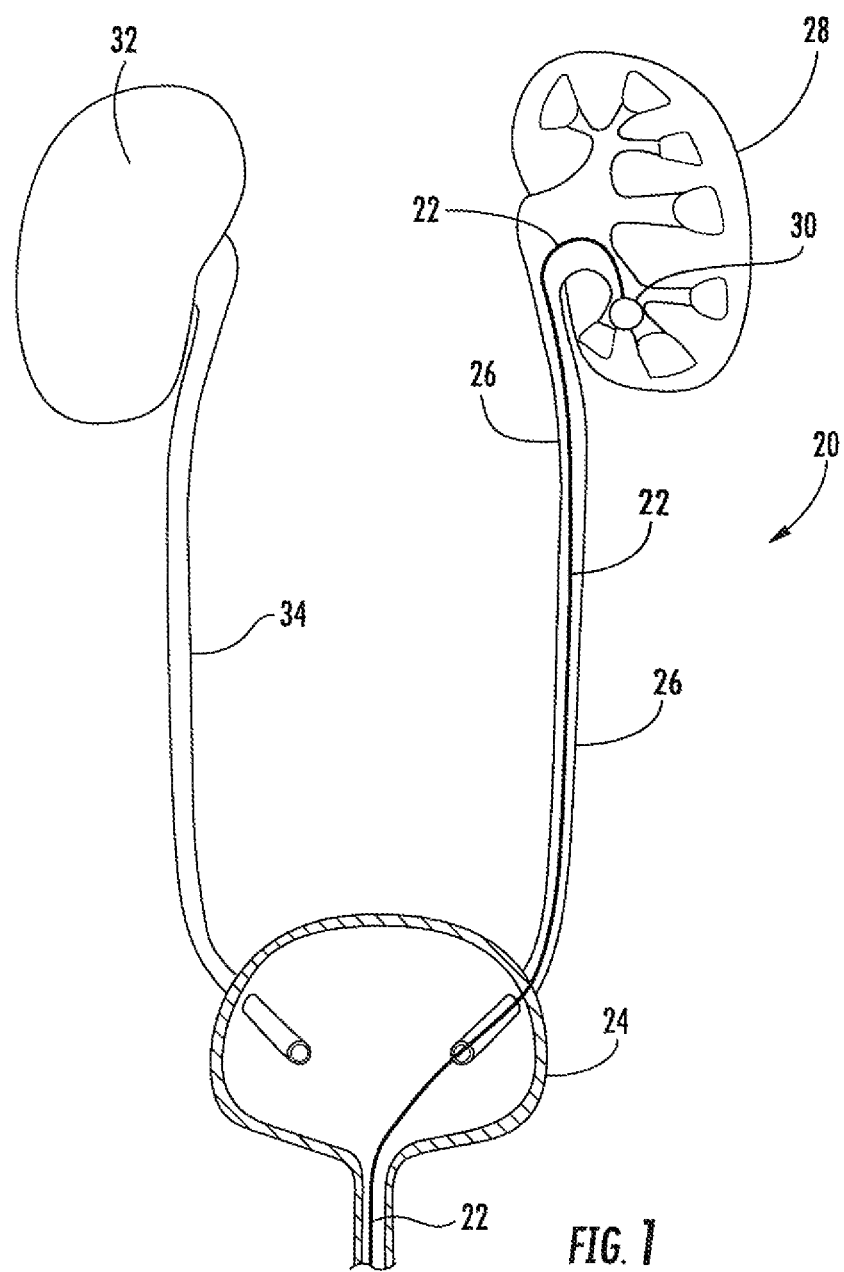
FIG. 1 illustrates a highly schematic and diagrammatic view of the invention in the context of its use for uteroscopic TFL lithotripsy.

FIG. 1 illustrates generally at 20 a highly schematic diagrammatic view of an ureteroscope 22 of the invention in the context of its use and inserted through the bladder 24 and ureter 26 into a longitudinally sectioned right kidney 28 and in contact with a kidney stone 30 in the lower pole of the kidney. The left kidney 32 of the pair and corresponding ureter 34 are also illustrated. The ureteroscope 22 may be deflected up to 270° so as to enter the lower pole of the kidney 28 without hindrance and in the substantial absence of damage due to bending that characterizes prior ureteroscopes.

Figure 2:
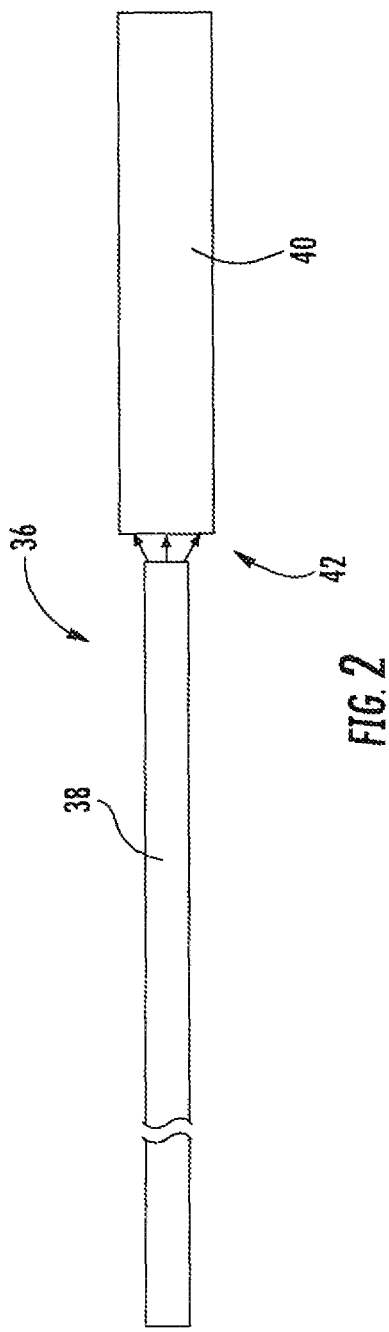
FIG. 2 illustrates a schematic image of the distal portion of continuous optical fiber having a tapered tip of the prior art methods for TFL lithotripsy.

FIG. 2 illustrates generally at 36 in a longitudinal and highly schematic plan view a combination of a distal portion of a trunk fiber 38 and detachable and replaceable wave guide tip 40 of the invention in optical connecting, light transmitting contact as indicated by the arrows, separated by a gap shown generally at 42 for dissipating heat. It is generally desirable to maintain a small air gap or other separation, including, for example, a light transmissive crystal, between the trunk fiber and a detachable wave guide tip, whether a fiber or hollow wave guide, to dissipate heat, so long as optical coupling contact is maintained between the wave guide tip and trunk fiber. The proximal end of the trunk fiber, not shown in this view, is connected to a laser for transmitting energy through the trunk fiber and ultimately through the detachable tip 40 to a hardened mass, including a urinary stone, in the practice of lithotripsy. The combination of trunk fiber 38 and wave guide tip 40 are housed within an endoscope tube, including the ureteroscope schematically illustrated in FIG. 1 but not illustrated in FIG. 2, in connection with the practice of the invention. In use, the wave guide tip extends beyond the distal terminus of the endoscope tube.

The trunk fiber 38 is designed to be relatively thin and flexible. Trunk fiber diameter normally is ≤200 μm and may range from about 50 to 200 μm. More typically, the diameter may be from about 100 to 150 μm, providing ultimate flexibility for the lithotripsy procedure and ease of entry into the lower pole of the kidney or other tight bodily cavities multiple times without damaging the trunk fiber and without having to replace the trunk fiber. Depending on the ureteroscope or other endoscope length, the trunk fiber 38 may vary in length from about 0.5 to 2 meters.

The detachable and disposable wave guide tips 40 may be a fiber tip or a hollow wave guide. When the detachable wave guide 40 is a fiber tip, then trunk fiber 38 and detachable fiber tip generally are made of the same or very similar materials as each other, including a low-OH silica core, cladding, and jacket, which are not separately illustrated. Single-use treatment tips may vary in diameter from 100 to 600 µm and from less than 0.5 to 5 cm in length, most commonly from 5 to 10 mm in length. The proximal end of a detachable wave guide tip 40, which is the end mounted adjacent the trunk fiber 38, including a hollow wave guide tip or a fiber tip that is in optical transmitting contact with the distal end of the small diameter trunk fiber, is generally of a size to efficiently transfer light energy from the distal end of the trunk fiber through the tip to the distal end of the tip and then to the stone or other hardened mass. Thus, the proximal end of the wave guide, in optical coupling contact with the distal end of the trunk fiber, will be of size compatible for efficient optical coupling with the trunk fiber. The disposable tip may be either cylindrical, in which event the proximal and distal ends are of similar diameter, typically about 300 µm in diameter, or tapered, in which case the distal end normally is of larger diameter than the proximal end. Typically, for a tapered tip, the ratio of the proximal to the distal end will be in a range of from about 1:2 to 1:3. For example, the detachable tip may have a proximal end of 100 µm and a distal end of about 200 µm to 300 µm. If the proximal end is 200 µm, then the distal end will be from 400 to 600 µm. The wider distal end of the tip provides a means to modify laser divergence to improve energy delivery to ablate a hardened mass, including a kidney stone.

It should be recognized that lithotripsy refers to any of several medical procedures in which a hardened mass within the body is physically altered so as to reduce the negative impact of the mass and, in many instances, to allow the mass to be removed or destroyed. Laser lithotripsy refers to lithotripsy using optical fibers as the delivery system to supply energy to the mass, and is most commonly performed with an endoscope, which is a flexible or semi-rigid device that typically includes a tubular section for insertion into a body cavity to locate a hardened mass for destruction. The tubular section often includes fiber optic illumination ports; a single working channel for irrigation and through which instruments can be inserted, including the treatment fiber; and a detector port through which the physician can visually observe the interior of the body cavity and locate the hardened mass. Endoscopic laser lithotripsy is commonly used for removal of kidney stones or gallstones or other hardened masses. Endoscopes for this purpose are often referred to as ureteroscopes.

Figure 3:
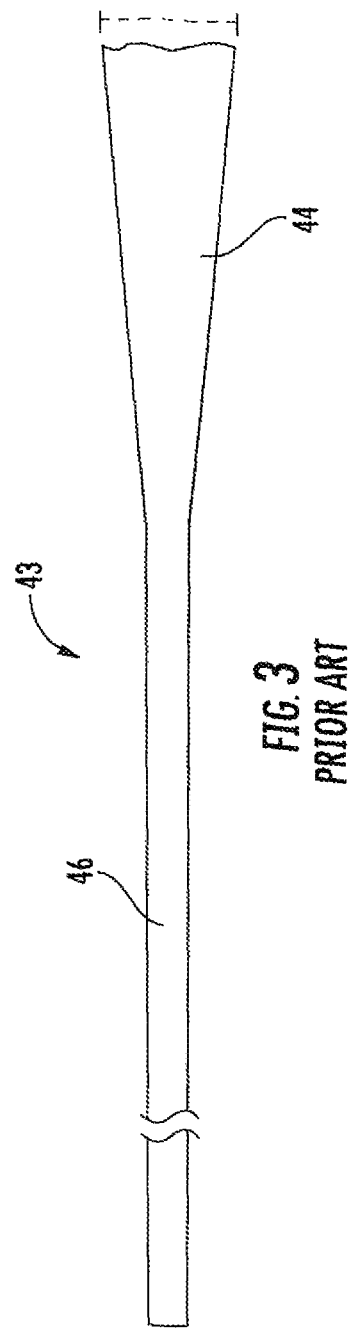
FIG. 3 illustrates in an exploded and highly schematic plan view the assembly of the invention of a tipless trunk fiber for TFL lithotripsy and a detachable wave guide tip.

For comparison, illustrated in FIG. 3 and labeled "Prior Art" is the distal tip portion of a 2 meter long continuous tapered fiber illustrated generally at 43, in which the fiber tip 44 is not detachable from and replaceable on the trunk 46 and has been used for the practice of TFL lithotripsy. The prior art continuous fiber 43 is similar in performance characteristics at similar diameters and taper to the detachable fiber tip and trunk fiber of the invention that were obtained from the same fiber source, FIG. 2. It is important to recognize that the distal tip of the prior art fiber 43 is not a separate, detachable portion from the trunk fiber and forms a continuous part of the same fiber, whereas the detachable distal tip 40 of the invention is a separate tip that is optically, but not physically, coupled to the trunk fiber 38, is detachable from the trunk fiber, and is replaceable for reuse of the trunk fiber and allowing for semi-permanent integration of endoscope and trunk fiber. The continuous fiber is subject to more frequent replacement of the entire fiber because of burn back during lithotripsy, whereas only the detachable tip of the invention needs to be replaced. Burn back is schematically illustrated at 47 in FIG. 3.

Figure 5:
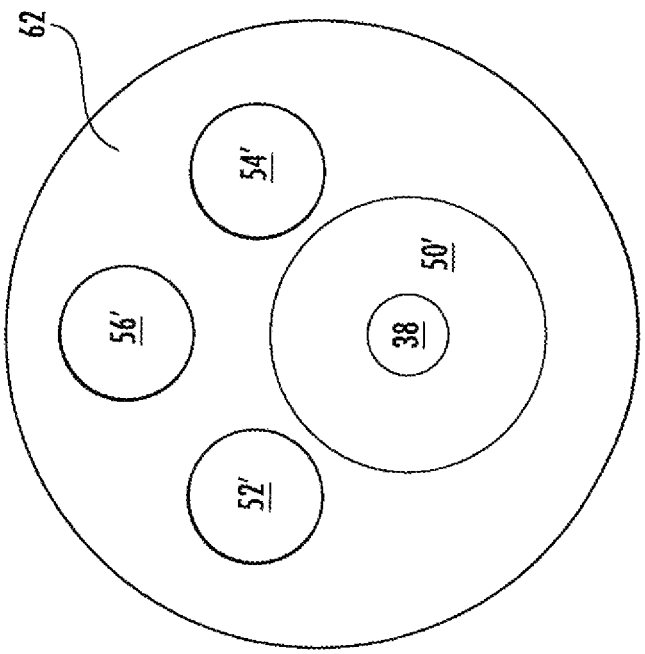
FIG. 5 illustrates in a highly schematic front plan view an endoscope cap having a trunk fiber of the invention located in the working channel of the endoscope.
Figure 4:
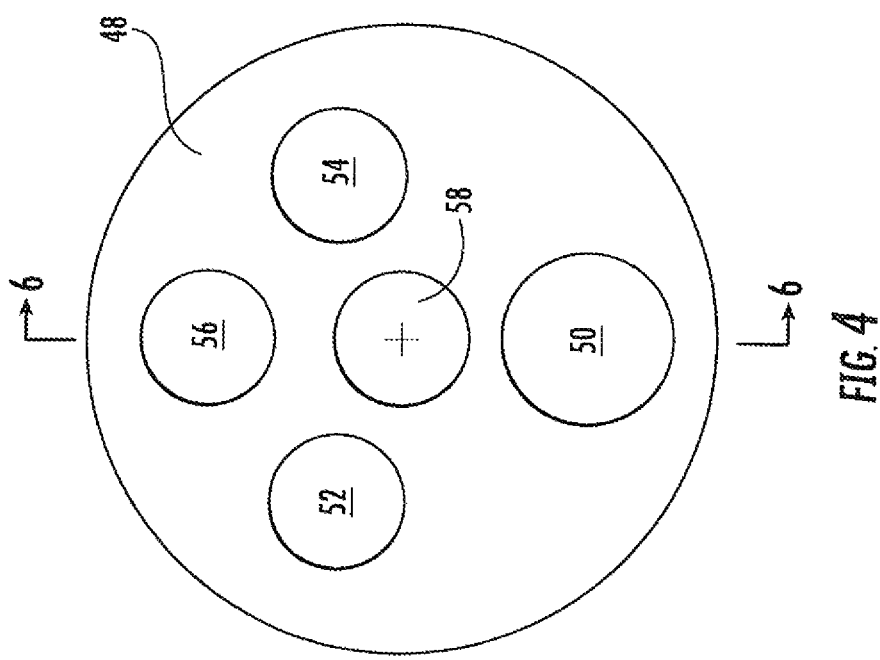
FIG. 4 illustrates in a highly schematic front plan view an endoscope cap of the invention having a dedicated axially centrally located channel for a trunk fiber for use in connection with laser lithotripsy.

FIGS. 4 and 5 illustrate diagrammatic plan views of two different face caps, 48 and 62, respectively, for the ureteroscope tubes of the invention, such as are illustrated at 22 in FIG. 1, and are broadly applicable to any endoscope for TFL lithotripsy. It should be readily understood that the face caps, sometimes called "endoscope tips," are not to be confused with the detachable wave guide tips of the invention as illustrated at 40, FIG. 2, and that are in optical connecting contact with a trunk fiber. Instead, the face caps 48, 62 form the removable terminus of the endoscope tube 22, FIG. 1, through which the detachable wave guide reaches a hardened mass, including kidney stones 30, FIG. 1. Face caps normally are small, stainless steel, generally cylindrical bodies having multiple channels, including illumination ports providing light guides, detector or magnification viewing ports through which the physician may view the body cavity from an eyepiece on the endoscope, and a working channel for irrigation, instruments, including for example, a stone basket for carrying away pieces of broken stones, and capable of being fitted in the irrigation channel with an optical fiber for supplying laser energy to a hardened mass. It should be understood that the endoscope face cap remains in place at the terminus of the flexible shaft of an endoscope during an endoscopic procedure, including TFL lithotripsy.

FIG. 4 illustrates a plan view of an ureteroscope face cap 48 for independent integration of a trunk fiber of the invention in a dedicated channel. The face cap extends axially a short distance to pressure fit snugly within a ureteroscope tube, not illustrated. The face cap has a working channel 50 through which irrigation is provided during the procedure and through which instruments may extend, a pair of illumination ports 52 and 54, and a viewing port 56 through which the physician may observe the lithotripsy procedure. A centrally located port 58 provides a channel for a tipless trunk fiber 38 of the invention (FIG. 2, not shown in FIG. 4) that is semi-permanently integrated into the ureteroscope tube for multiple sterilizations and uses. It should be recognized that port 58 need not be centrally located, although central location provides for ease and convenience in aligning the hardened mass and wave guide tip and for aligning the wave guide tip and trunk fiber. Centrally locating a channel and port for the optical fiber may require reducing the size of the working channel from about 1.0 mm to about 0.4 to 0.6 mm.

FIG. 6 illustrates generally at 49 a longitudinal section through a highly schematic side plan view of an endoscope tube face cap 48. taken along line 6-6 of FIG. 4 and bisecting the face cap. Dedicated channel 58 contains trunk fiber 38, not shown, to provide optical coupling contact with a wave guide 40, indicated by the arrows across the air gap illustrated generally at 42. Mechanisms for securing the trunk fiber and wave guide in optical coupling contact are discussed in more detail below beginning with FIG. 7.

FIG. 5 illustrates a plan view of a more conventional ureteroscope face cap 62 having the viewing port 56' and illumination ports 52' and 54' similar to those of FIG. 4, and also having a tipless trunk fiber 38 of the invention (see also, FIG. 2) integrated into the approximately 1.0 mm working channel 50' of the ureteroscope. It should be recognized that the tipless trunk fiber 38 may, if desired, be located in one of the illumination ports 52' or 54' or in the viewing port 56', although not necessarily with equivalent results.

FIG. 7 illustrates generally at 60 a partially exploded, partially broken away longitudinal plan view of one embodiment of an optical fiber assembly of the invention including a mechanism for optical connection of a trunk fiber 38 and a detachable and replaceable wave guide 40 (FIG. 2), which in this embodiment is a cylindrical fiber tip of the invention, shown generally at 62. Assembly 60 includes a terminal portion of a small diameter trunk fiber 38 having concentric layers of flexible plastic hypodermic tubing, shown generally at 64 an including layers 64' and 64" circumscribing the trunk fiber and a flexible stainless steel hypodermic sleeve 66 circumscribing the hypodermic tubing 64. A rigid connector assembly shown generally at 68 circumscribes the stainless sleeve 66 for joining in optically transmitting contact the small diameter trunk fiber 38 and the larger diameter detachable fiber tip illustrated generally at 62.

Turning now to a discussion of the detachable larger diameter fiber tip illustrated generally at 62, the tip fiber 63 is stripped of its jacket at the working end 70 because the jacket will burn during lithotripsy. The tip fiber 63 has a flexible hypodermic tubing 72 opposite the working end for fitting within the connector assembly 68 and stainless sleeve 66 circumscribing the trunk fiber. A key 74 is provided attached to the hypodermic tubing 72 adjacent the proximal end of the detachable fiber tip to provide a locking mechanism upon insertion of the fiber tip 62 into the connector assembly 68.

FIG. 8A illustrates in additional detail a longitudinal partial sectional view of the embodiment of the connecting apparatus 60 shown in FIG. 7 for optically coupling the distal end of the terminal portion of trunk fiber 38 (FIG. 7) with the proximal end of disposable distal tip 62. The connecting apparatus is a spring-loaded, twist-locking, and keyed releasable retaining mechanism, assembly 60, for uniting a trunk fiber of uniform diameter with a detachable tip fiber of uniform diameter. Connecting apparatus assembly 60 includes, on the trunk fiber 38 side, a flexible stainless steel sleeve 66 tightly circumscribing a flexible hypodermic tubing 64 that in turn circumscribes the trunk fiber 38 (FIG. 7). It should be noted that the portion of trunk fiber 73 shown in FIG. 8A and circumscribed by a spring 75 is stripped of its jacket to avoid burning of the jacket. Rigid stainless connector sleeve 68 provides a concentric and rigid structure of about 2 cm in length. The outside diameter of the connector sleeve was reduced to 1.00 mm, which is 1,000 μm, for fitting inside a typical ureteroscope working channel, which normally has an inside diameter of 1.19 mm, or 1,190 μm.

A commercially available spring 75 having an inside diameter of 400 μm and an outside diameter of 600 μm was inserted into the stainless steel hypodermic sleeve 66 and mounted over the stripped portion 73 of the trunk fiber, abutting against the transverse surface of the terminus of the hypodermic tubing 64. Smaller gage springs, if available, could potentially be used. It is important to note that the spring length in a relaxed condition is sufficient to reach from the terminus of the sleeve 64 to beyond the terminus of the stripped fiber sheath 73 so that when the detachable tip fiber 62 is inserted the spring will be compressed sufficiently to secure the tip fiber in a locked-in-place condition.

A J-groove channel shown generally at 78 was carefully machined into the stainless steel sleeve 66 extending from just beyond the distal terminus of the sleeve for receiving the proximal end of the key 74 on the detachable tip and locking the key into place, via a locking notch 78a, forming the "J" in the J-groove channel. Key 74 is a length of 36 gauge wire axially and adhesively mounted to the proximal end of the tubing circumscribing the detachable fiber tip.

Turning now to FIG. 8B, in operation, the proximal end of the detachable fiber tip 62/72 is inserted into the tubing 66 against the force of the spring 75 and rotated to engage the key 74 with the J-groove 78 (FIG. 8A) in sleeve 66. When released, the force of the spring secures the key in the J-groove. The overall insertion distance of the detachable tip into the tubing was 5 mm followed by a 90 degree clockwise rotation and release of spring tension against the key in the locking notch. The spring length and the depth of the J-groove are controlled to maintain the trunk fiber and detachable tip in close proximity sufficient for optical coupling contact, but not direct physical contact. A small air gap provided between the trunk fiber and detachable distal fiber tip, created by the combination of spring, key, and locking notch, reduces coupling damage by precluding optical divergence from overfilling the proximal end of the detachable tip. The length of locking notch controls the width of the air gap, which was 0.3 mm in this instance. The overall insertion distance of the detachable tip into the tubing can vary from about 3 to 7 mm to provide an air gap of from about 0.2 to 0.4 mm.

All the components of the spring-loaded, twist-locking design were scaled and secured together with a conservative amount of a biocompatible adhesive. The entire detachable portion of the system, including detachable tip fiber and key, was of 10 cm in length and could be manually deflected up to 45° without optical transmission failure, demonstrating that the trunk/tip interface provided efficient laser beam coupling without misalignment under bending conditions. The polyimide tubing sheath and thin steel tubing on the trunk fiber remained flexible. Only about 2 cm of that region around the trunk/tip interface, created by coupling apparatus and comprising stainless tubing, remained rigid and inflexible, though within an overall outside diameter of 1 mm to fit within the working channel of a typical ureteroscope or for use in a dedicated central channel or other channel.

Table 1 below, summarizes the components used for the assembly of the trunk fiber and detachable tip illustrated in FIGS. 7, 8A, and 8B.

TABLE 1

Materials used to assemble detachable fiber optic tip. All dimensions for inner(ID), outer diameter (OD), and cut length are in millimeters.

|  | Part | ID (mm) | OD (mm) | Length |
|---|---|---|---|---|
| Trunk | Fiber core | n/a | 0.195 | 2,000 |
|  | Tubing | 0.200 | 0.203 | 40 |
|  | Spring | 0.400 | 0.600 | 4 |
|  | J-groove tubing | 0.643 | 0.795 | 25 |
|  | Cover tubing | 0.838 | 1.270' | 20 |
| Tip | Fiber | n/a | 0.370 | 50 |
|  | Tubing (P) | 0.455 | 0.607 | 15 |
|  | Key | n/a | 0.125 | 2.5 |

Note:
(S) Stainless steel;
(P) Polyimide;
(ID) Inner diameter;
(OD) outer diameter;
(n/a) not applicable;
(PM) Polymicro, Phoenix, AZ;
(AS) Amazon Supply, Seattle, WA;
(LS) Lee Spring, Greensboro, NC;
(PW) Powerwerx, Brea, California' °Filed down to an OD of ~1.00 mm FIGS. 9(A) and 9(B) illustrate yet another embodiment for a connector assembly of the invention illustrated generally at 80 and in which a trunk fiber 73 is optically connected to a detachable tapered fiber tip 82 which may be a cylindrical tip 63 (FIG. 7), if desired, through a self-centering spring-loaded hollow, cylindrical sleeve, the rigid outer housing of which is illustrated at 84. FIG. 9(A) is illustrated with the fiber tip locked in place and FIG. 9(B) with the fiber tip inserted partially and in an unlocked position. Sleeve 84 is adhered to the tapered fiber tip 74 at the proximal end of the tip and extends from the tip to receive the trunk fiber 38/73. The entire assembly of connector sleeve and detachable tip measures about 1 cm from end-to-end. The trunk and tip fibers are as previously described, and the tip fiber may be detachable cylindrical or detachable tapered, as desired.

In operation, rigid sleeve 84 circumscribes a spring-biased rubber grommet 86 adjacent the trunk fiber 38 over a jacketed portion thereof, the spring circumscribing a channel for the fiber tip at the opposite end. Insertion of the distal end of the stripped trunk fiber tip 73 into the sleeve against the force of the spring 89 compresses the spring so that grommets 86 retain the trunk fiber. A small air gap 90 between the proximal end of the tapered fiber tip and the distal end of the trunk fiber improves power transmission by dissipating heat. To unlock the sleeve, pressure is applied to compress the spring via the sleeve, release the grommet, and remove the sleeve and fiber tip.

Figure 10A:
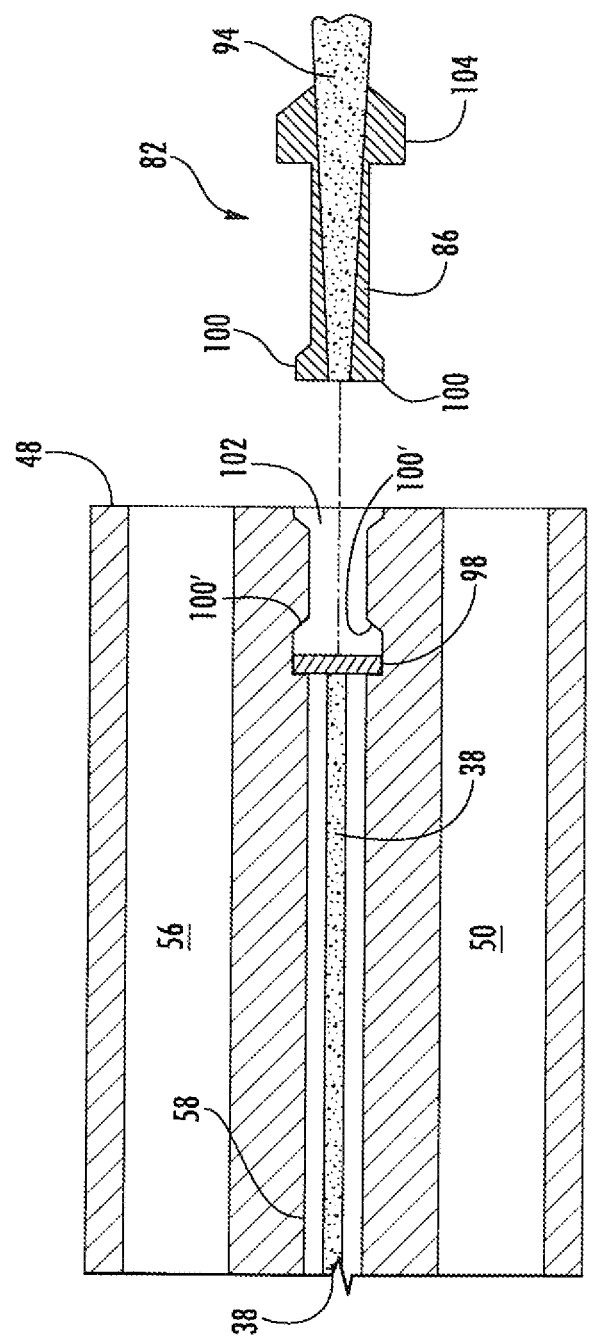
FIG. 10A illustrates a longitudinal section through an exploded assembly of a tapered tip fiber and an end cap for an endoscope having an axially centrally-located trunk fiber where the detachable tip is to be retained in a snap-in and snap-out relation in a receptacle in the end cap.

FIGS. 10A and 10B are directed to detachable fiber tips provided in a cork-like design illustrated generally at 82 for pop-in and pop-out optical connecting contact with a trunk fiber 38 semi-permanently mounted in an endoscope and extending into face cap 48. FIG. 10(A) is an exploded sectional view; FIG. 10(B) is the assembled trunk fiber and tapered fiber combination. In this embodiment, the trunk fibers are mounted in a dedicated channel 58 rather than in the working channel 50. The dedicated channel is axially and centrally located, which is considered advantageous; although other locations may be suitable. For example, one illumination port 52 or 54 (FIG. 4), could be dedicated to this purpose.

The cork-like design 92 comprises a tapered fiber 94 mounted within a rigid stainless steel hollow sleeve 96 of about 2.0 mm in length. The fiber tip may extend beyond the sleeve distally of the endoscope tip, as illustrated. This embodiment may use an integrated trunk fiber 38 of 50 to 100 µm in diameter mounted in a dedicated channel illustrated at 58, not the working channel 50, and that optionally may terminate at the endoscope tip in a protective crystal sapphire window 98. The sapphire window establishes a gap between the trunk fiber and the tip. The tapered tip and stainless sleeve assembly 92 may be snapped in place via resilient flexible projections 100 on the sleeve 96 that are received in reciprocal fittings 100' in the entry 102 to the dedicated channel for the trunk fiber and against the terminus of which entry the tapered tip is provided a flange 104 that the physician may grasp to remove the cork-like tip assembly 92.

Figure 11:
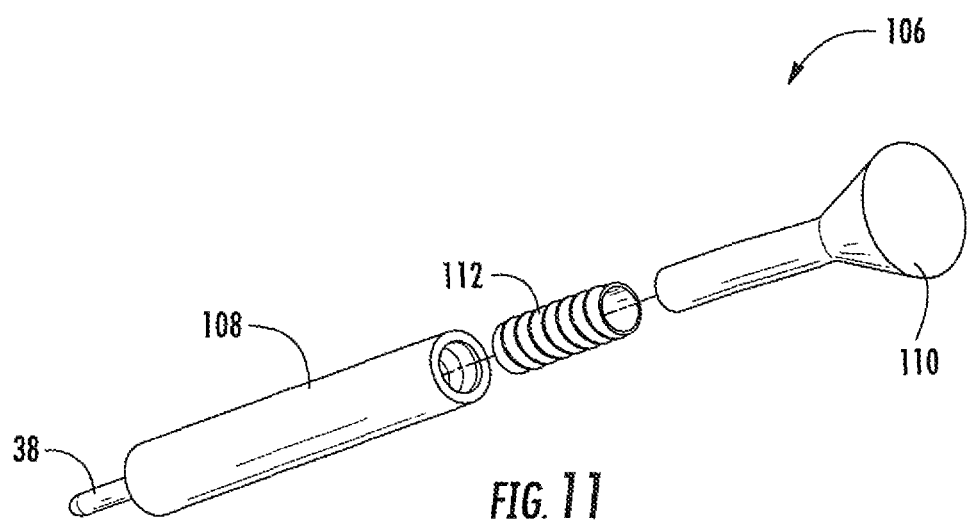
FIG. 11 illustrates a perspective and exploded view of a tapered detachable fiber tip of the invention, an externally threaded retaining sleeve; and an internally threaded mated receiving sleeve mounted over the distal end of the trunk fiber.

Turning now to an alternative embodiment illustrated in FIG. 11, FIG. 11 illustrates in an exploded partial perspective view an alternative connector assembly, illustrated generally at 106. A 100 µm core or other suitable diameter optical trunk fiber 38 for TFL lithotripsy is inserted into and adhesively mounted onto a stainless steel cylindrical tube 108, which is internally threaded at a distal portion extending beyond the insertion of the trunk fiber. It should be recognized that the trunk fiber is selected for illustrative purposes and that smaller or larger trunk fibers may be used in the practice of the invention, from 50 to 200 µm, more typically from 100 to 150 µm, as discussed elsewhere in this specification. Threaded tube 108 should preferably be flexible and, together with trunk fiber 38, forms a semi-permanent mounting in an ureteroscope or other endoscope. By "semi-permanent" is meant that the combination of ureteroscope or other endoscope with the trunk fiber and tube installed is intended for multiple uses in different patients over time without replacement of the trunk fiber and without shortening the trunk fiber through cleaving or degradation. The uteroscope and trunk fiber can be sterilized as a unit between patients.

The tapered fiber tip 110 is adhesively attached to an externally threaded cylindrical member 112 that can matingly engage the internally threaded tube 108 to place the tip and trunk fibers in optical connecting contact. The tapered fiber tip 110 has a length of about 0.5 to 1 cm so that the tip will be protected within the flexible ureteroscope as the ureteroscope navigates the urinary tract. However, longer tips can be selected, from about 0.5 to up to 5 cm, and most commonly from about 5 to 10 mm. The proximal end of the tapered fiber tip 110 is a 150 µm core fiber that is adhesively inserted into the externally threaded tube 112 at one end thereof for threaded attachment to internally threaded tube 108. It should be recognized that the size of the proximal end of the tapered tip is selected for efficient optical transmission with trunk fiber 38, which in this instance has a core of 100 µm, and that the criteria and size ranges can be selected based on similar factors as discussed above in connection with the cylindrical fiber tips of other embodiments.

A small air gap, similar to that described in connection with other embodiments, is maintained between the trunk and tip fibers on assembly to improve power transmission and to reduce fiber damage by dissipating heat. The tapered fiber tip 110 expands to 300 µm at the distal end thereof. The fiber tip may be cylindrical, in which the proximal and distal ends are of similar diameter, typically about 300 µm in diameter, or tapered as shown in FIG. 1, in which case the distal end normally is of larger diameter than the proximal end. Typically, for a tapered fiber tip, the ratio of the proximal to the distal end will be in a range of from about 1:2 to 1:3. For example, the detachable tip may have a proximal end of 100 µm and a distal end of about 200 µm to 300 µm. If the proximal end is 200 µm, then the distal end will be from 400 to 600 µm. The wider distal end of the fiber tip provides a means to modify laser divergence to improve energy delivery to ablate the hardened mass.

Figure 12:
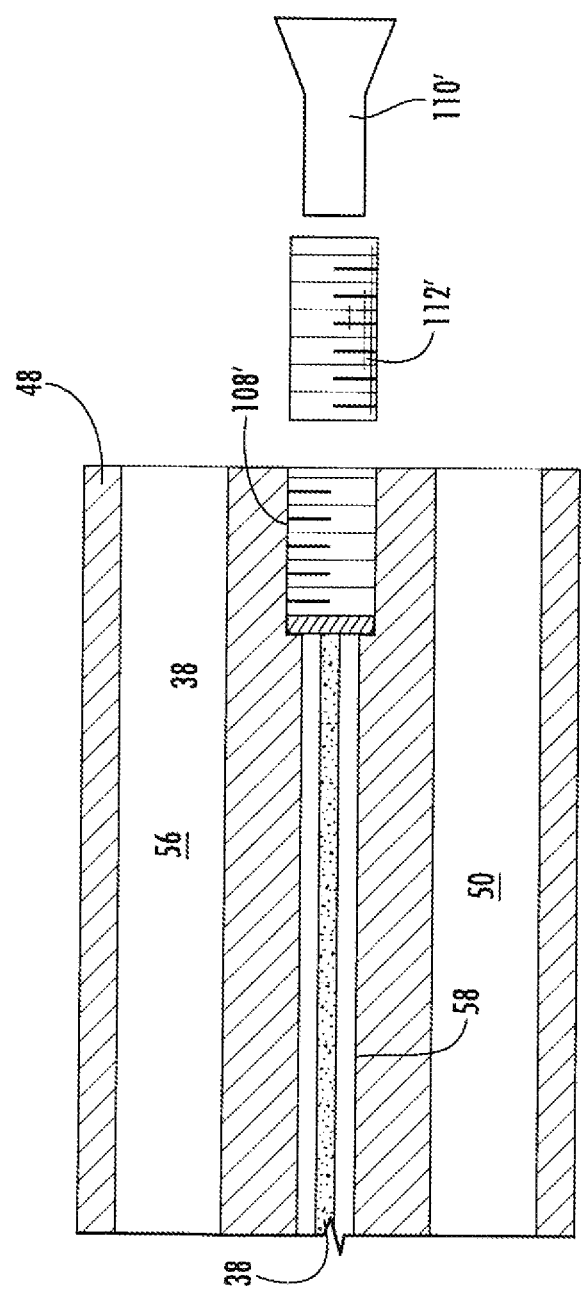
FIG. 12 illustrates a longitudinal section through an exploded view of a tapered detachable fiber tip of the invention, an externally threaded retaining sleeve, and an end cap for an endoscope having an axially centrally-located trunk fiber where the detachable tip is to be retained in an internally threaded mated receiving sleeve adjacent the distal and of the trunk fiber.

FIG. 12 illustrates generally at 114 a somewhat similar embodiment to that of FIG. 11 in that an externally threaded member 112' is used to attach the tapered fiber tip 110' to an internally threaded member 108' in connection with the trunk fiber. However, it should be recognized that internally threaded member 108' is mounted in a face cap 48 at the end of an endoscope and terminates in a sapphire crystal 98 to provide a gap (42, FIG. 2) between the trunk and tip fibers while maintaining optical connection.

A tapered detachable fiber tip is adhesively secured internally of a metal cylindrical sheath using, for example a biocompatible heat-resistant epoxy. Approximately 1.2 mm of the detachable fiber tip is secured internally of the metal sheath, which is of about 2.5 mm in length.

It should be recognized that in certain embodiments, a simple slip fit of the detachable tip in optical connection with the trunk fiber, secured by an easily dissolvable biocompatible adhesive, may be sufficient. The physician could employ a solvent during the lithotripsy procedure to quickly dissolve the adhesive to remove a damaged tip and then adhesively secure a fresh tip to continue the procedure. In these embodiments, the trunk fiber typically would be semi-permanently integrated into the endoscope tube and the channel in the endoscope tip would be defined so that a tip fiber and sheath combination would, upon insertion, reach a stop to maintain a suitable air gap for heat dissipation, as previously described in connection with earlier embodiments.

Figure 16:
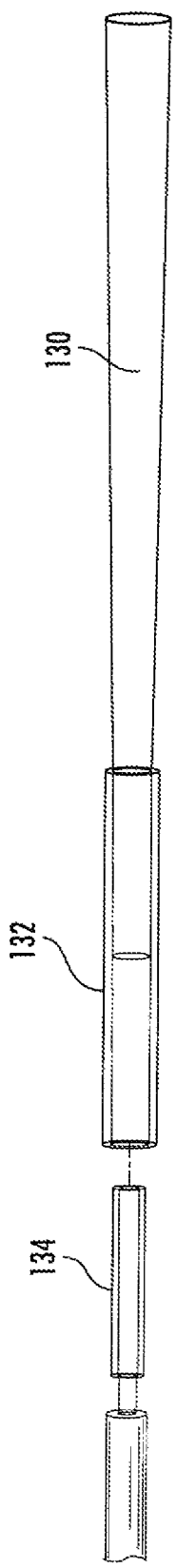
FIG. 16 illustrates a partial sectional view through an exploded assembly of a trunk fiber having a permanent magnet circumscribing the distal end of the trunk fiber for magnetically adhering the trunk fiber to a tapered fiber tip.
Figure 17:
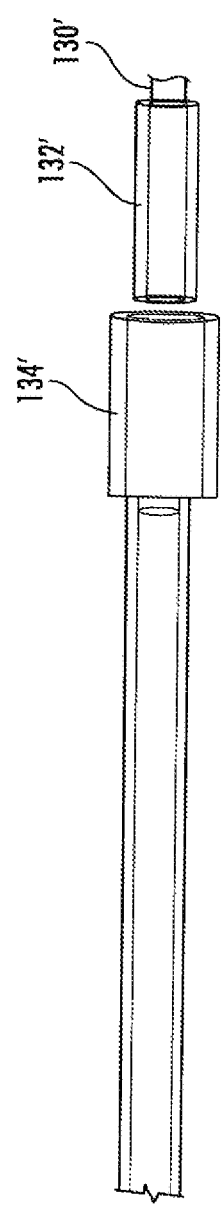
FIG. 17 illustrates in a partial sectional view an alternative magnet arrangement to that of FIG. 16.
Figure 18:
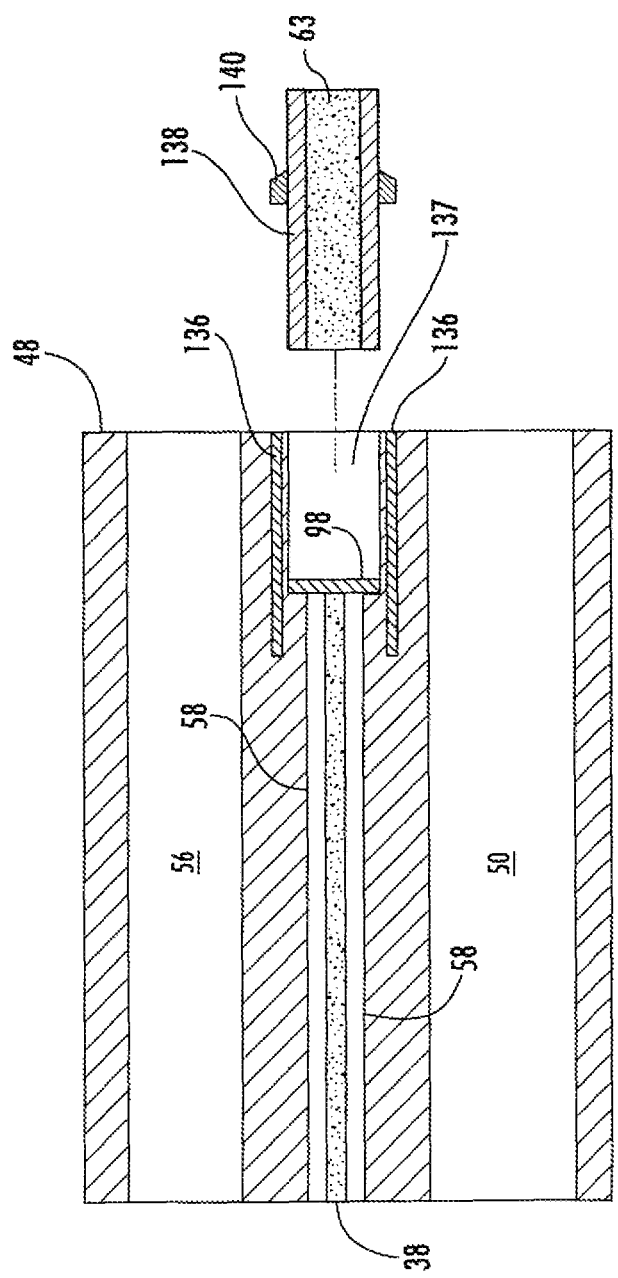
FIG. 18 illustrates a longitudinal section through an exploded view of a detachable fiber tip of the invention, a metal retaining sleeve, and an end cap for an endoscope having an axially centrally-located trunk fiber where the detachable tip is to be retained in a mated receiving sleeve adjacent the distal end of the trunk fiber and having permanent magnets mounted in the end cap about the distal end of the end cap.

FIGS. 13, 14, 15, 16, 17, and 18 illustrate additional concepts for fiber-to-fiber connectors based on either electromagnet magnets (FIG. 13, 14, or 15) or permanent magnets (FIGS. 16, 17, and 18).

FIGS. 13, 14, and 15 illustrate a design shown generally in a longitudinal perspective view at 120 in FIG. 13 and using an electromagnetic attachment in which an electrically powered electromagnetic coil 122 of relatively weak power sufficient to secure the fiber tip 124 and to provide for ready removal and replacement, is mounted about a rigid stainless steel jacket 126 circumscribing the distal end of the trunk fiber. The coil is powered via electrical connection to the input and output connectors 125 and 127 through the endoscope tube (not shown), and the rigid metal sleeve extends beyond the electromagnet over a distal most portion of the trunk fiber stripped of its jacket. Upon insertion of the stripped portion 73 of the distal most end of the trunk fiber and circumscribing rigid metal sleeve 126 into a corresponding circumscribing stainless steel sleeve 128 on the proximal end of the detachable tip, then the electromagnet causes the rigid stainless members to be secured magnetically.

FIGS. 16 and 17 are directed to the use of permanent magnets to couple trunk fibers to tapered tips or non-tapered, cylindrical tips 130, 130'. Tips 130, 130' are adhesively mounted into stainless steel sleeves 132, 132' for receiving (132, FIG. 16) or insertion into (132', FIG. 17) a corresponding mating sleeve 134, 134' associated with the trunk fiber. If one of these sleeves is permanently made magnetic, the assembly can be secured.

FIG. 18 is similar, but illustrates an endoscope face cap 48 having a dedicated channel 137 to receive a detachable tip fiber 63 having a metal jacket 138 with finger flanges 140 for ease of insertion and removal. Channel 137 is circumscribed at least in part by permanent magnets 136 selected to retain fiber tip 63 and housing 138 and to provide for ease of removal. Channel 137 terminates in a sapphire crystal to provide a gap so that coupling contact is maintained between the trunk fiber 38 in dedicated channel 58 opposite the channel 137.

FIGS. 19A, 19B, and 19C are directed to detachable and extruding hollow wave-guide tips 145 provided in a cork-like design for pop-in and pop-out optical connecting contact with a trunk fiber 38 semi-permanently mounted in an endoscope. In this embodiment, the trunk fibers are mounted in a dedicated channel 58 rather than in the working channel 50 (FIG. 4) and it should be recognized that for convenience only the dedicated channel 58 is illustrated. The wave guide 145 can comprise a highly polished stainless hollow cylinder or hollow silica fiber having a stainless jacket. The wave guide is mounted within a dedicated receiving channel 150 in an endoscope tip into which protrudes a stripped portion 73 of the trunk fiber that may be surrounded by a sapphire crystal 151 to provide and maintain a suitable gap. When in place, the trunk fiber 73 extends into the wave guide via hollow space 146 in the wave guide body. Similar to the embodiments of FIGS. 10A and 10B, the stainless sleeve may be snapped in place via resilient flexible projections 148 on the sleeve. Against the terminus of the entry 150 the hollow wave guide is provided a stop on insertion. A pneumatic channel 150 is provided parallel to the trunk fiber channel 58 that joins the space 150. Once the wave guide is secured in place in the dedicated channel, the physician is able remotely to provide air through the pneumatic channel to push the wave guide to extrude from the endoscope tip to engage a hardened mass, the projections on the hollow wave guide securing the wave guide in place in the channel. Typically, the physician would extrude the wave guide as a kidney stone is viewed and the ablation procedure started. In this embodiment, not only is the trunk fiber preserved, but the detachable tip may not have to be replaced as often as for some other embodiments.

Urinary stones comprised of calcium oxalate monohydrate are the most common type of stone operated upon and were used to demonstrate the functionality and practicality of a detachable fiber tip of the invention in comparison to the prior art continuous silica fiber used for laser lithotripsy. 95% pure calcium oxalate monohydrate (COM) urinary stone samples from humans were obtained for the purpose of comparing stone ablation rates of the detachable fiber tip to the continuous and tapered fiber tip. Stone samples ranged from 8 to 15 mm in diameter and from 150 to 500 mg in mass, with an average mass of 250 mg. Initial dry stone mass was recorded with an analytical balance before securing the stone in place with a clamp and submerging it into a saline bath. Either a prior art continuous, low —OH silica fiber or a detachable silica fiber tip of the invention was held manually in direct contact with the submerged stone. Laser pulse energy of 30 mJ was delivered to the stone surface in contact mode through the prior art continuous fiber tips and the detachable fiber tips. The fiber was gently scanned over the stone surface during laser irradiation to keep the fiber in constant contact with the stone. A total of 6000 pulses were delivered to each stone sample, for a total ablation time of either 1 or 2 minutes, with 100 or 50 pulses per second, respectively. The stones were then dried in an oven at 70° C. for over 30 minutes before taking final dry mass measurements.

The distal tip, whether in the continuous prior art fiber or a detachable fiber tip of the invention, degrades or experiences burn-back during stone fragmentation. Two fiber degradation studies were performed to study the trends and causes of fiber burn-back. First, microscopic images of the distal fiber tips were taken after stone ablation to analyze fiber burn-back as a function of laser pulse rate and temporal pulse configuration. The detachable fiber tips and tapered fibers were illuminated with a white light lamp from the proximal end.

Comparison of fiber tip roughness to the number of pulses during stone ablation was also performed. Surface roughness for short-length detachable fiber tips in a vertical orientation can be measured with a tabletop interferometer. Surface roughness measurements were performed using a scanning white light interferometer and a 50× magnification objective. A spherical fit to the profile was removed because the fiber tips were slightly convex due to the fiber polishing process. The cladding was 2 µm longer than the silica center. The fiber was initially polished and measured, then re-measured after stone ablation to analyze fiber tip roughness.

For the detachable fiber tip, the measured input and output pulse energy was 38.4 and 30.7 mJ, respectively, yielding a 79.9% transmission. In contrast, the pulse energy output for the prior art continuous tapered fiber measured 35.2 mJ for the same input energy, yielding a 91.7% transmission. The detachable fiber tip had four silica/air interfaces while the continuous tapered fiber tip only had two, which may be responsible, in part, for this difference. Theoretical optical transmission rates for the detachable and continuous tapered fiber tips were calculated to be 87.3% and 93.3%, respectively, based on a Fresnel reflection loss of 3.25% at each silica/air interface and a reported 0.014 dB attenuation through a 2-m-long fiber at λ=1908 nm. For silica, n=1.44, and for air, n=1. Nevertheless, even with somewhat lower transmission, the detachable silica fiber tip compares favorably to the continuous fiber.

COM stones (comprising calcium oxalate monohydrate) were ablated with the detachable fiber tip of the connector assembly of FIG. 12(a) at a maximum rate of 187 μg/s using the 20-Hz (packet) pulse profile at 30 mJ. The table below shows the mean ablation rate based on five stone samples for each set of laser parameters. For consistency, the stones were not fragmented into smaller stones by the laser. All stone mass loss was the result of stone vaporization with particle sizes less than 100 μm. Contrary to the temperature rise results, stone ablation rates for both fibers tended to favor the pulse packets rather than the standard pulse rates, and no statistical difference between ablation rates for stones was observed whether using detachable or tapered fibers.

TABLE

Calcium oxalate monohydrate (COM) stone ablation rates for detachable and tapered fiber tips as a function of laser pulse rate and profile.

| Pulse profile | Pulses/s* | Detachable tip (/'9/s) | Tapered lip (/<9/s) |
|---|---|---|---|
| 50 Hz | 50 | 50 ± 15 | 47 ± 9 |
| 10 Hz | 50 | 108 ± 13 | 94 ± 22 |
| 100 Hz | 100 | 113 ± 8 | 92 ± 37 |
| 20 Hz | 100 | 187 ± 37 | 175 ± 31 |

Degradation of the detachable fiber lip was studied in two ways. First, after stone ablation, minimal degradation was observed for 50 Hz, while the 100 and 10 Hz (packet) profiles showed signs of pitting. Significant burn-back was seen at 20 Hz (packet) for both detachable and tapered fiber tips. This trend was consistent with the stone ablation rates.

Second, to better understand the fiber burn-back mechanism, a more rigorous fiber tip roughness analysis was also performed. Measured fiber tip roughness before and after delivery of 60,000 total laser pulses at 50 Hz is equivalent to 20 minutes, or five times longer, than the 12,000 pulse tip degradation. The root-mean-squared (Rq) roughness parameter only changed from 4.72 to 4.77 nm, and the average roughness (Ra) changed from 3.35 to 3.48 nm, which is essentially identical for the detachable tapered fiber tip and the continuous tapered fiber tip.

The connector assembly of FIGS. 7, 8(A), and 8(b) for adjoining the detachable fiber tip to the trunk fiber has an overall diameter of 1.00 mm (3.0 Fr), which is smaller than the diameter of the working channel of a typical flexible ureteroscope of 1.19 mm (3.6 Fr). The design can be scaled down by using a smaller spring. A smaller diameter spring than 75, FIG. 8(A), can be machined from stainless steel tubing. Polyimide tubing is likely to be too flexible. The J-groove channel 78, which is stainless steel, provides support for the spring pressure and multiple tip exchanges.

The length of the detachable tip with spring-loaded locking mechanism, as illustrated in FIGS. 7, 8(A), and 8(B) aids in manually grasping the device for ex-vivo stone ablation testing. The lengths of all the device components can be reduced to increase overall flexibility for use inside an ureteroscope working channel and for inserting an assembly of a trunk fiber and detachable tip combination, if needed, through the working channel during the procedure and without hindering ureteroscope deflection. Heat resistant and biocompatible adhesives provide for clinical use and re-sterilization as needed.

The detachable fiber tips in accordance with the invention performed within 90% of their theoretical optical transmissions, which is at least equivalent to conventional fibers having tapered tips. Proximal coupling, polishing artifacts, debris from fabrication, or poor concentricity between the trunk and tip fibers may result in somewhat poorer performance of the detachable fiber tip and trunk fiber assembly as compared to the commercially available tapered fiber during ex vivo testing. However, the saline environment encountered during lithotripsy generally can be expected to improve index matching and overall optical transmission.

Temperature rise in the fibers, whether continuous tapered tip fiber or trunk fiber with a detachable tip fiber, has been observed to be a function of total pulses per second rather than the pulse configuration. The detachable fiber tip and trunk fiber assembly did not reach a surface temperature above 50° C., which is important because above this temperature, the heated fiber potentially could harm the patient if in contact with soft tissues. Heating of the continuous tapered tip fiber, whether at the tip or trunk surface portion, was generally somewhat less than that for the detachable fiber tip and at the interface between the tip and trunk fiber assembly. The commercially available continuous tapered fibers were flat-polished by the manufacturer and so the tips were not as steep-angled as for the detachable tips. On the other hand, the short fiber lengths of the detachable tips were polished in fiber holders designed for much longer fibers, resulting in steeper-angled tips. Steeper-angled tips divert more back reflection into the cladding of the fiber, thus causing more heat buildup. The heat generated at the detachable fiber tip is thus believed to be an artifact of experiment in which back-reflected light from the distal tip overfills the trunk fiber upon return. Also, the tip was attached in optically coupling contact that included an air gap region between the two fibers, the trunk fiber and the detachable tip. Reflections in the air gap between the two fibers are believed to also contribute to the temperature rise. An index-matching fluid could be expected to reduce differential heating and would need to be selected as a biocompatible fluid having a high optical damage threshold.

Another factor impacting the results reported is that the thermal profiles were taken in air, not in saline irrigation fluid. During a lithotripsy procedure, the fibers would be immersed in a saline irrigation environment. A saline irrigation environment would be expected to provide cooling. A saline/silica interface at the fiber tip, whether of the tapered fiber or the detachable fiber tip, would be expected to reduce back reflection, which back reflection is believed to be a primary cause of undesirable heating. Additionally, both the detachable and the tapered fiber tips would be extruded from the ureteroscope during stone ablation, thus making distal fiber tip heating less significant than heating at the detachable fiber tip interface with the trunk fiber.

It should be noted that the tapered distal fiber tip has a smaller numerical aperture of 0.055 compared to the detachable fiber tip. The smaller numerical aperture is due to the change in modal structure and focusing in the tapered region. The far field spatial beam profiles thus are less significant to lithotripsy procedure than the surface profiles. Since cavitation bubbles serve as the conduit for the laser energy to the stone, divergence or numerical aperture might play a small role in energy density as the light reaches the stone surface, depending upon the fiber's distance to the stone, which is not constant. Thus the tapered fiber still offers a slight advantage over a straight fiber because the energy density or spatial beam size is more uniform beyond the fiber distal tip.

What is claimed is:

1. An endoscopic system for lithotripsy comprising:
    a. an endoscope housing comprising a tube for insertion into a body cavity of a lithotripsy patient, the tube of the endoscope housing comprising at least one channel for an optical treatment fiber; and
    b. an optical treatment fiber contained within the channel of the endoscope housing and in optically coupling contact with a laser source, the optical treatment fiber comprising:
        i. a trunk fiber having proximal and distal ends, the core of the trunk fiber having a diameter of from about 50 to 200 μm, the trunk fiber in optically coupling contact with the laser source at the proximal end of the trunk fiber and in optically coupling contact with a detachable wave guide at the distal end of the trunk fiber;
        ii. a detachable wave guide having a length of from about 0.5 to 5 cm and in optically coupling contact with the trunk fiber at the distal end of the trunk fiber, the detachable wave guide adapted for extending from the tube of the endoscope housing for laser lithotripsy of a hardened mass; and
        iii. a connector assembly for releasably retaining the trunk fiber and the detachable-wave guide in optically coupling contact;
    wherein upon damage to the detachable wave guide during lithotripsy, the endoscope tube may be withdrawn from the patient and the damaged detachable wave guide may be removed from the tube of the endoscope housing and replaced with another detachable wave guide; and
    wherein the detachable wave guide has a core diameter of from about 100 μm to 600 μm and is tapered in increasing diameter from a proximal end adjacent to the trunk fiber to a distal end remote from the trunk fiber in a ratio of from more than about 1:1 to 1:3.

2. The endoscopic system of claim 1 wherein the detachable wave guide is in spaced apart optically coupling contact with the distal end of the trunk fiber.

3. The endoscopic system of claim 1 wherein the detachable wave guide is separated from the distal end of the trunk fiber by a predetermined gap of 0.2 to 0.4 mm.

4. The endoscopic system of claim 1 wherein the detachable wave guide is a detachable fiber tip that is 5 to 10 mm long.

5. The endoscopic system of claim 1 wherein the detachable wave guide is a cylinder having a core of about 300 μm diameter.

6. The endoscopic system of claim 1 wherein the core of the detachable wave guide is tapered in increasing diameter from a proximal end adjacent the trunk fiber of about 100 μm to a distal end of about 300 μm.

7. The endoscopic system of claim 1 wherein the core of the detachable wave guide is tapered in increasing diameter from a proximal end adjacent the trunk fiber of about 200 μm to a distal end of from about 400 to 600 μm.

8. The endoscopic system of claim 1 wherein the trunk fiber is about 0.5 to 2 meters long.

9. The endoscopic system of claim 1 wherein the connector assembly is of diameter ≤1.0 mm.

10. The endoscopic system of claim 1 wherein the detachable wave guide is a hollow wave guide.

11. The endoscopic system of claim 1 wherein the endoscope system comprises a flexible ureteroscope for treatment of kidney stone disease.

* * * * *